(12) United States Patent
Yada et al.

(10) Patent No.: US 7,348,455 B2
(45) Date of Patent: Mar. 25, 2008

(54) PROCESS FOR PRODUCING (METH)ACRYLIC ACIDS

(75) Inventors: Shuhei Yada, Yokkaichi (JP); Yasushi Ogawa, Yokkaichi (JP); Yoshiro Suzuki, Yokkaichi (JP); Kiyoshi Takahashi, Yokkaichi (JP); Kenji Takasaki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 416 days.

(21) Appl. No.: 10/859,221

(22) Filed: Jun. 3, 2004

(65) Prior Publication Data

US 2004/0220426 A1    Nov. 4, 2004

Related U.S. Application Data

(63) Continuation of application No. PCT/JP02/12709, filed on Dec. 4, 2002.

(30) Foreign Application Priority Data

| Dec. 4, 2001 | (JP) | 2001-369636 |
| Dec. 5, 2001 | (JP) | 2001-371608 |
| Dec. 18, 2001 | (JP) | 2001-385168 |
| Dec. 25, 2001 | (JP) | 2001-392058 |
| May 16, 2002 | (JP) | 2002-141162 |
| May 16, 2002 | (JP) | 2002-141194 |

(51) Int. Cl.
*C07C 51/16* (2006.01)
*C07C 57/02* (2006.01)

(52) U.S. Cl. ........................ 562/545; 562/549; 562/595

(58) Field of Classification Search .................... None
See application file for complete search history.

(56) References Cited

U.S. PATENT DOCUMENTS

| 3,666,794 A * | 5/1972 | Otsuki et al. .................. 560/4 |
| 5,458,414 A | 10/1995 | Crump et al. |
| 5,504,247 A | 4/1996 | Saxer et al. |
| 5,734,075 A | 3/1998 | Fauconet et al. |
| 5,847,050 A | 12/1998 | Toritani et al. |
| 6,252,110 B1 | 6/2001 | Uemura et al. |
| 6,420,498 B1 | 7/2002 | Konaka et al. |
| 6,436,245 B1 * | 8/2002 | Nishimura et al. ........... 203/99 |
| 6,482,981 B2 | 11/2002 | Ueno et al. |

FOREIGN PATENT DOCUMENTS

| EP | 0 780 360 B1 | 6/1997 |
| EP | 0 887 334 A1 | 12/1998 |
| JP | 4-90839 | 3/1992 |
| JP | 7-48311 | 2/1995 |
| JP | 8-183756 | 7/1996 |
| JP | 8-225486 | 9/1996 |
| JP | 9-71603 | 3/1997 |
| JP | 9-183753 | 7/1997 |
| JP | 10-298132 | 11/1998 |
| JP | 11-12222 | 1/1999 |
| JP | 2000-262880 | 9/2000 |
| JP | 2001-139605 | 5/2001 |
| JP | 2001-199931 | 7/2001 |
| JP | 2002-60402 | 2/2002 |

* cited by examiner

*Primary Examiner*—Paul A. Zucker
(74) *Attorney, Agent, or Firm*—Oblon, Spivak, McClelland, Maier & Neustadt, P.C.

(57) ABSTRACT

A process for producing (meth)acrylic acid or (meth)acrylic acid esters, which comprises a reaction step comprising vapor phase catalytic oxidation of propylene, propane or isobutylene and, if necessary, a reaction step comprising an esterification step, characterized in that at the time when a high boiling mixture (hereinafter referred to as a high boiling material) containing a Michael addition product, is decomposed in a decomposition reactor to recover (meth) acrylic acids, while forcibly imparting a liquid flow in the circumferential direction to a liquid reaction residue in the decomposition reactor, the liquid reaction residue is discharged. In a process for recovering a valuable substance by thermally decomposing the high boiling material containing the Michael addition product of (meth)acrylic acids, it is possible to transfer the decomposition residue from the decomposition reactor to the storage tank without clogging, whereby a long-term continuous operation is possible.

16 Claims, 11 Drawing Sheets

LINE 2-1 IN FIG. 3

LINE 5 IN FIG. 1, OR LINE 1 IN FIG. 2

AA: FRACTIONATING COLUMN
BB: LIGHT COMPONENT SEPARATION COLUMN
CC: EXTRACTION COLUMN
DD: ESTERIFICATION REACTION COLUMN
EE: ACETIC ACID SEPARATION COLUMN
FF: SOLVENT SEPARATION COLUMN
GG: COLLECTION COLUMN
HH: ALCOHOL RECOVERY COLUMN
II: SOLVENT RECOVERY COLUMN

PROCESS FOR PRODUCING AN ACRYLIC ESTER
(TWO STEP OXIDATION METHOD OF PROPYLENE)

PP : COOLED LIQUID TANK (1)

(2)

(1)

(2)

PROCESS FOR PRODUCING (METH)ACRYLIC ACIDS

TECHNICAL FIELD

The present invention relates to an industrially advantageous process for producing (meth)acrylic acids at a high recovery rate, while reducing the amount of industrial wastes, by decomposing byproducts such as Michael addition products of (meth)acrylic acid or (meth)acrylic esters, by-produced in a step for producing (meth)acrylic acids, and recovering variable compounds such as (meth)acrylic,acid, (meth)acrylic esters and alcohols.

In this specification, "(meth)acrylic acid" is a general term for acrylic acid and methacrylic acid, and it may be either one or both of them. Further, "(meth)acrylic acids" is a general term for these acids and (meth)acrylic esters obtainable from such acids and alcohols, and the term is meant for one comprising at least one of them.

BACKGROUND ART a. As a method for decomposing Michael addition products by-produced during production of acrylic acid or acrylic esters, it is common to employ a thermal decomposition method using no catalyst in the case of a process for producing acrylic acid (JP-A-11-12222), while in the case of a process for producing an acrylic ester, a method is known to carry out the decomposition by heating in the presence of a Lewis acid or a Lewis base (JP-A-49-55614, JP-B-7-68168, JP-A-9-110791, JP-A-9-124552, JP-A-10-45670). Further, as a decomposition reactive system for Michael addition products, it is common to employ a reaction distillation system wherein the desired decomposed reaction product is distilled by distillation while carrying out the decomposition reaction. Further, a method is also known wherein Michael addition products by-produced in a step for producing acrylic acid, and Michael addition products by-produced in a step for producing an acrylic ester, are put together, followed by thermal decomposition. There are a method for thermal decomposition by a reactive distillation system in the absence of any catalyst (JP-A-8-225486) and a method for decomposition by means of a highly concentrated acid catalyst (JP-A-9-183753).

In order to increase the recovery rate of acrylic acid, an acrylic ester or an alcohol useful as a product or as a raw material for a reaction, at the top of such a decomposition reaction column, it is necessary to increase the decomposition reaction temperature and to suppress the bottom discharge amount, whereby there has heretofore been a problem such that the bottom liquid tends to be a highly viscous liquid; as the decomposition temperature is high, an oligomer or polymer of acrylic acid or an acrylic ester being an easily polymerizable substance, is likely to form; and some of substances contained in the raw material for the reaction tend to precipitate, whereby a solid will deposit at the bottom of the decomposition reaction column, a polymer is formed due to a liquid contained in the deposit, and such a deposit will flow into a liquid discharge line at the time of an operational change thereby to cause sudden clogging of the liquid discharge line; and thus, there has been no appropriate method whereby the decomposition reaction column can be operated constantly for a long time. Especially when a solid has once deposited at the bottom of a decomposition reaction column, an easily polymerizable liquid occluded in the deposited solid tends to be extremely polymerizable since it can not flow, and the decomposition reaction temperature is relatively high, thus leading to a phenomenon where the amount of the deposit will be further increased by such polymerization. Thus, it has been desired to cope with this problem.

b. As an example to solve this problem, a method is conceivable wherein the diameter of a pipe to transfer the bottom liquid is reduced to transfer the liquid at a high flow rate, but it has been impossible to adopt such a method, since the pump for such a transfer is required to be of a high pressure type, such being economically disadvantageous as an industrial production method. Further, a method is also conceivable wherein in order to lower the viscosity of the bottom liquid, waste liquid from the production step may be added or water may be added afresh, but such will bring about a decrease of the liquid temperature, whereby clogging tends to be rather accelerated, or it tends to be required to add such water in a large amount. Accordingly, it has been practically impossible to adopt such a method.

c. On the other hand, as is well known, there is a vapor phase oxidation method of propylene as a reaction to form acrylic acid. For such a method of obtaining acrylic acid by oxidizing propylene, there are a two step oxidation process wherein oxidation to acrolein and a next step of oxidation to acrylic acid, are carried out in separate reactors, respectively, since the oxidation conditions are different, and a process wherein oxidation to acrylic acid is carried out directly by one step oxidation.

FIG. 9 shows an example of a flowchart for forming acrylic acid by two step oxidation, followed by a reaction with an alcohol to form an acrylic ester. Namely, propylene, steam and air are subjected to two step oxidation via the first and second reactors packed with e.g. a molybdenum-type catalyst to form an acrylic acid-containing gas. This acrylic acid-containing gas is contacted with water in a collection column to obtain an aqueous acrylic acid solution, which is extracted in an extraction column by adding a suitable extraction solvent, whereupon the extraction solvent is separated in a solvent separation column. Then, acetic acid is separated in an acetic acid separation column to obtain crude acrylic acid, and in a fractionating column, a byproduct is separated from this crude acrylic acid to obtain a purified product of acrylic acid. Further, this acrylic acid (purified product) is esterified in an esterification reaction column, and then, via an extraction column and a light component separation column, a crude acrylic ester is obtained. From this crude acrylic ester, a byproduct (high boiling product) is separated in a fractionating column to obtain a purified product of an acrylic ester.

Here, depending upon the type of the acrylic ester, there may be a case where the flow sheet will be as shown in FIG. 10. In such a case, the byproduct is obtained as bottoms in an acrylic acid separation column.

In the process for producing an acrylic ester in FIG. 10, acrylic acid, an alcohol, recovered acrylic acid and a recovered alcohol are respectively supplied to an esterification reactor. This esterification reactor is packed with a catalyst such as a strongly acidic ion exchange resin. An esterification reaction mixture comprising a formed ester, unreacted acrylic acid, an unreacted alcohol, formed water, etc., withdrawn from this reactor, will be supplied to an acrylic acid separation column.

From the bottom of this acrylic acid separation column, the bottom liquid containing unreacted acrylic acid is withdrawn and recycled to an esterification reactor. A part of this bottom liquid is supplied to a high boiling component separation column, whereby a high boiling component is separated from the bottom, and this is supplied to and decomposed in a high boiling component decomposition reactor (not shown). The decomposition product containing a valuable substance formed by the decomposition will be recycled to the process. A place in the process where the decomposition product is recycled, varies depending upon the process conditions. High boiling impurities such as polymers will be discharged from the high boiling decomposition reactor to the exterior of the system.

From the top of this acrylic acid separation column, an acrylic ester, an unreacted alcohol and formed water are distilled. A part of the distillate is recycled as a reflux liquid to the acrylic acid separation column, and the rest is supplied to an extraction column.

To this extraction column, water for extraction of an alcohol is supplied. Water containing an alcohol, flowing out of the bottom, will be supplied to an alcohol recovery column. The distilled alcohol will be recycled to the esterification reactor.

A crude acrylic ester discharged from the top of the extraction column will be supplied to a light boiling component separation column, and a light boiling material is withdrawn from the top and recycled within a process. A place within the process where it is recycled, varies depending upon the process conditions. The crude acrylic ester having the low boiling material removed, will be supplied to a purification column for an acrylic ester product, whereby a high purity acrylic ester will be obtained from the top. The bottom liquid contains a large amount of acrylic acid and therefore is recycled within the process. The place within the process where it will be recycled, varies depending upon the process conditions.

Further, in recent years, instead of a solvent extraction method wherein recovery of acrylic acid from the above aqueous acrylic acid solution is carried out by means of an extraction solvent, an azeotropic separation method is carried out wherein distillation is carried out by means of water and an azeotropic solvent, so that from the top of the azeotropic separation column, an azeotropic mixture comprising water and the azeotropic solvent, is distilled, and from the bottom, acrylic acid is recovered.

Further, also practically used is a method wherein acrylic acid is obtained by using propane instead of propylene and using a Mo—V—Te type composite oxide catalyst or a Mo—V—Sb type composite oxide catalyst. In the case of methacrylic acid and a methacrylic ester, isobutylene or t-butyl alcohol is employed instead of propylene, and a purified product of methacrylic acid and a purified product of a methacrylic ester are obtained via a similar oxidation process and the subsequent esterification process.

Further, as a method for forming a (meth)acrylic ester (an acrylic ester or a methacrylic ester), a method is practically employed wherein a (meth)acrylic ester of a lower alcohol and a higher alcohol are subjected to a transesterification reaction by using e.g. an acid as a catalyst, to produce a (meth)acrylic ester of the higher alcohol. The crude (meth) acrylic ester obtained by this transesterification exaction, is subjected to steps such as catalyst separation, concentration and fractionation to obtain a purified (meth)acrylic ester.

A useful byproduct such as a Michael addition product, is contained in the fraction separated by distillation and purification of the above-mentioned crude acrylic acid, the crude methacrylic acid, the crude acrylic ester or the crude methacrylic ester. Accordingly, this byproduct is decomposed to recover (meth)acrylic acid or its ester, or the raw material alcohol.

Heretofore, the methods as disclosed in the above a have been known as methods for decomposing a Michael addition product by-produced during production of acrylic acid or an acrylic ester. Thus, heretofore, it has been common to decompose a Michael addition product by-produced during production of an acrylic ester thereby to recover a valuable substance such as acrylic acid, an acrylic ester or an alcohol. As such a decomposition and recovery method, it has been common to employ a reactive distillation system wherein distillation is conducted while carrying out a decomposition reaction.

To carry out the reactive distillation system, a reactor provided at its upper portion with a distillation column, is employed. As such a distillation column, it is common to employ a plate column provided internally with various trays, or a packed column having various packing materials packed, in order to bring about fractionating effects. The plates may, for example, be bubble cap trays, uniflux trays, flexible trays, ballast trays, perforated trays (sieve trays), chimney trays, ripple trays, dual flow trays or baffle trays. The packing material may, for example, be a ring-type packing material such as Raschig rings, spiral rings or pall rigns, or a saddle type packing material such as Berl saddle or interlock saddle, or others such as Goodloe packing, Dixon ring, MacMahon packing, or a vertically flat plate type regulated packing material.

However, in both production processes for acrylic acid and an acrylic ester, the raw material to be supplied to the step of decomposing the byproduct, is a fraction obtained by concentrating a high boiling component formed in the reaction system or purification system. Further, acrylic acid and acrylic esters are very easily polymerizable materials, and consequently, the raw material for the decomposition reaction contains polymers formed. Further, the decomposition reaction is carried out at a high temperature, and therefore, there will be a polymer formed during the decomposition reaction. Accordingly, it is likely that a solid substance is already present in the raw material to be subjected to decomposition, and even when no solid substance is present in the raw material, it may precipitate anew, or there may be a solid substance to be formed during the distillation separation operation or in the decomposition step where a chemical reaction is simultaneously carried out. And, adhesion, deposition or accumulation of such a solid substance takes place on the trays or at void spaces of the packing material in the distillation column, whereby an increase of the differential pressure, deterioration of the gas/liquid contact state and further clogging, may, for example, occur. Consequently, there has been a problem that such tends to hinder to obtain a high recovery rate of a valuable substance or tends to hinder a constant continuous operation.

Accordingly, in both processes for producing acrylic acid and the ester, it is desired to solve the above problems and to develop a process for decomposing a Michael addition product, whereby a high recovery rate can constantly be obtained.

d. Further, in a method for recovering (meth)acrylic acid or a (meth)acrylic ester by carrying out the decomposition reaction of a Michael addition reaction product by-produced during the process for producing (meth)acrylic acid or a (meth)acrylic ester, if the decomposition reaction temperature is made high in order to obtain a high recovery rate for such (meth)acrylic acid, a (meth)acrylic ester or an alcohol, an oligomer or polymer of (meth)acrylic acid or a (meth) acrylic ester being an easily polymerizable substance, will be formed. To prevent such polymerization, it is suggested to add molecular oxygen in addition to a polymerization inhibitor such as hydroquinone, methoxyhydroquinone, phenothiazine or hydroxylamine, to the decomposition reactor (e.g. the above-mentioned JP-A-10-45670, paragraphs 0012 and 0019).

However, if such a method is employed, there may sometimes be a case where not only no adequate effect for preventing polymerization of (meth)acrylic acid or a (meth) acrylic ester in the decomposition product by oxygen is obtainable, but also polymerization may be accelerated, and thus there may be a case where the above decomposition reaction can not be constantly continued over a long time.

e. Further, an acrylic acid-containing gas obtained by vapor phase catalytic oxidation by molecular oxygen of propylene and/or acrolein, usually contains maleic acid, as one of byproducts, in an amount of from about 0.2 to 1.6 wt %, based on acrylic acid. Maleic acid is a dicarboxylic acid represented by $HOCO-CH=CH-CO_2H$ and is in an equilibrium state with a carboxylic anhydride having one molecule of water dehydrated in its molecule in its solution. Hereinafter, unless otherwise specified, maleic acid and maleic anhydride will be together represented by maleic acid. When an acrylic acid-containing gas is collected by a solvent in the form of an acrylic acid-containing solution, maleic acid will be collected at the same time. The boiling point of maleic acid is high as compared with acrylic acid, and in the purification step by distillation, maleic acid will be concentrated in the bottoms.

When two molecules of acrylic acid undergo Michael addition, an acrylic acid dimer will be formed. There is no means to prevent formation of such an acrylic acid dimer in the acrylic acid solution, and the formation speed increases as the temperature becomes high. Further, a higher oligomer such as an acrylic acid trimer will sequentially be formed by acrylic acid and an acrylic acid dimer. In the purification step for acrylic acid, an acrylic acid dimer (or oligomer) will be formed mostly in the distillation column where heating is carried out, particularly at the bottom portion where the temperature is high, and the retention time is long.

In order to improve the recovery rate of acrylic acid in the purification step, it is usual to recover acrylic acid from the formed acrylic acid oligomer.

As a recovery method from an acrylic acid oligomer, there may, for example, be a method wherein thermal decomposition is carried out under reduced pressure in the presence or absence of a catalyst, and acrylic acid is recovered as a distilled gas or a distilled liquid, as disclosed in JP-B-45-19281. In such a case, the distilled gas and the distilled liquid of acrylic acid contains a large amount of high boiling compounds other than acrylic acid to be recovered, such as maleic acid. In a case where the operation temperature is increased in order to increase the recovery rate of acrylic acid, the maleic acid concentration in the recovered acrylic acid will also be increased.

As a method to reduce such maleic acid, in a method as disclosed in JP-A-11-12222, a crude acrylic acid containing from 3 to 10 wt % of maleic acid and other acrylic acid oligomers, is introduced into an acrylic acid recovery column, and acrylic acid is distilled from the top, and the bottom liquid is thermally decomposed, and such a bottom liquid is recycled to the recovery column, whereby maleic acid can be reduced to a level of from 0 to 3 wt %.

In such a thermal decomposition recovery method of an acrylic acid oligomer, maleic acid as an impurity is disposed as bottoms of the thermal decomposition reaction apparatus or the distillation apparatus. At that time, if the amount of maleic acid contained in the recovered acrylic acid is large, the amount of maleic acid recycled in the system will increase, whereby instruments and the heat load in the purification step will increase. The simplest method to prevent this, is to reduce the thermal decomposition recovery amount of the acrylic acid oligomer, but the recovery rate for acrylic acid in the purification step will thereby be decreased, and the economical efficiency will be deteriorated.

In order to accomplish improvement of the recovery rate of acrylic acid and reduction of the recycling amount of maleic acid, there is a method of adding a distillation column as in the method disclosed in JP-A-11-1222. However, since acrylic acid is an easily polymerizable compound, it is common to carry out distillation under reduced pressure to prevent polymerization by lowering the operational temperature, but as the boiling point of maleic acid is higher than acrylic acid, even if the operation pressure is lowered, an increase of the operational temperature can not be avoided. This will not only facilitate clogging of the distillation apparatus by polymerization, but also tends to accelerate formation of an acrylic acid oligomer in the acrylic acid recovered by thermal decomposition. Further, in order to increase the vacuuming degree of the distillation installation, the diameter of the distillation column is increased, whereby the load during the construction and operation will also increase.

Further, concentrated maleic acid is discharged from the bottom. However, maleic acid is solid at room temperature and thus has problems such that the viscosity of the liquid tends to be high from the lower portion to the bottom of the distillation column, and deterioration in the separation ability due to fouling, or deposition of a polymer or clogging is likely to result.

Such problems result as maleic acid being an impurity is separated as a high boiling substance by distillation.

In order not to include a step of concentrating maleic acid by distillation and to improve the thermal decomposition recovery efficiency of acrylic acid, it is necessary to carry out, without imparting a large heat as distillation, either 1 reducing the maleic acid concentration in the acrylic acid solution to be supplied to the thermal decomposition reaction apparatus, or 2 reducing maleic acid in the acrylic acid solution recovered from the thermal decomposition reaction apparatus.

f. Further, heretofore, in an installation for producing acrylic acid or the like, it has been common to carry out a pressure measurement by installing a high pressure side detection portion of a liquid level meter in direct connection to the main body of the instrument. However, by a conventional method for installation of a liquid level meter, a polymerization inhibitor to be used for the preparation of an easily polymerizable compound or a formed polymer, is supplied to the high pressure side detection portion of the liquid level meter, and a solid substance is likely to be accumulated, whereby an error operation of the liquid level meter used to be observed.

Accordingly, it used to be difficult to carry out accurate measurement continuously by a liquid level meter, whereby it has been difficult to carry out a constant operation of the installation for a long period of time.

DISCLOSURE OF THE INVENTION a. It is an object of the present invention to overcome the problems in the conventional decomposition reaction of a Michael addition product of acrylic acid or an acrylic ester thereby not to let deposition remain in the decomposition reaction column, to prevent formation of a polymer in the decomposition reaction column and to prevent sudden clogging of the discharge pipe, so that a stabilized operation method is presented.

b. Further, it is an object of the present invention to provide a method for decomposing a byproduct during production of (meth)acrylic acids, whereby at the time of recovering a valuable substance by decomposing, by a reactive distillation system, a Michael addition product by-produced in the process for producing (meth)acrylic acid or a (meth)acrylic ester, adhesion, deposition or accumulation of such a solid substance is prevented, a high recovery rate of (meth)acrylic acid, a (meth)acrylic ester and an alcohol can be constantly maintained, and a constant continuous operation can be carried out for a long period of time.

c. Further, it is an object of the present invention to provide a method to eliminate recycling of maleic acid in an acrylic acid purification system involving thermal decomposition and recovery of an acrylic acid oligomer formed in the distillation purification step of an acrylic acid-containing liquid and to readily accomplish the purification without a problem of polymerization of acrylic acid or clogging of an equipment in the purification step.

d. Further, it is an object of the present invention to provide a method for installing a liquid level meter on an installation for producing an easily polymerizable compound, whereby accurate measurement can continuously be carried out by preventing formation and accumulation of a solid substance of the liquid to be measured at a high pressure side detection portion of the liquid level meter.

The present inventors have conducted various studies to accomplish the above objects, and as a result, have arrived at the present invention having the following gists.

(1) A process for producing (meth)acrylic acids, which comprises a method of decomposing in a decomposition reactor a high boiling mixture formed as a byproduct during the production of (meth)acrylic acids, characterized in that the high boiling mixture contains a Michael addition product having water, an alcohol or (meth)acrylic acid added to a (meth)acryloyl group; while forcibly imparting a liquid flow in the circumferential direction to a liquid reaction residue in the decomposition reactor, the liquid reaction residue is discharged; and (meth)acrylic acid or a (meth)acrylic ester is recovered.

(2) The process according to the above (1), characterized in that the liquid flow in the circumferential direction is imparted by stirring vanes installed in the decomposition reactor.

(3) The process according to the above (1), characterized in that the liquid flow in the circumferential direction is imparted by a liquid supplied from the exterior of the decomposition reactor.

(4) The process according to the above (3), characterized in that the liquid supplied from the exterior of the decomposition reactor is the high boiling material supplied as raw material, or a return liquid of the liquid reaction residue discharged from the decomposition reactor.

(5) The process according to any one of the above (1) to (4), characterized in that the liquid reaction residue is intermittently discharged from the decomposition reactor.

(6) The process according to any one of the above (1) to (5), characterized in that at the time of recovering a valuable substance by carrying out distillation as well as thermal decomposition of the high boiling mixture, the distillation is carried out by means of a distillation column which is internally provided with disk-and-donut type trays.

(7) The process according to any one of the above (1) to (6), characterized in that an oxygen-containing gas is added to a distillate from the decomposition reactor.

(8) The process according to any one of the above (1) to (7), characterized in that from a liquid to be supplied to the thermal decomposition reactor or from a liquid recovered from the thermal decomposition reactor, maleic acid contained in said liquid, is precipitated and separated.

(9) The process according to any one of the above (1) to (8), characterized in that a liquid level meter is installed on the thermal decomposition reactor, and a high pressure side detection line of the liquid level meter is connected to a liquid discharge line of the decomposition reactor.

The above present invention has the following preferred embodiments (a) to (f).

a1. A process for producing (meth)acrylic acids, which is a process for producing acrylic acid or (meth)acrylic acid (these are hereinafter generally referred to also as (meth)acrylic acid) or a (meth)acrylic ester ((meth)acrylic acid and a (meth)acrylic ester may hereinafter generally referred to also as (meth)acrylic acids), by a reaction step comprising vapor-phase catalytic oxidation of propylene, propane or isobutylene, and, if necessary, further by a reaction step comprising an esterification step, characterized in that at the time when a high boiling mixture (hereinafter referred to as a high boiling material) containing a Michael addition product, is decomposed in a decomposition reactor to recover (meth)acrylic acids, while forcibly imparting a liquid flow in the circumferential direction to a liquid reaction residue in the decomposition reactor, the liquid reaction residue is discharged.

a2. The process according to the above a1, wherein the liquid flow in the circumferential direction is imparted by stirring vanes installed in the decomposition reactor.

a3. The process according to the above a1 or a2, wherein the stirring vanes are anchor vanes, multistage puddle vanes, multistage inclined puddle vanes or lattice vanes.

a4. The process according to the above a1 or a2, wherein the structure of the stirring vanes is such that on a rotary shaft vertically installed at the center portion of the reactor, radial flow type vanes are attached in two or more stages in the rotational axis direction, so that vanes adjacent in the rotational axis direction are in a positional relation to the rotational axis direction such that their phases are displaced from each other by not more than 90°, and the lowest portion of the upper stage one of the vanes adjacent in the rotational axis direction, is located below the highest portion of the lower stage one.

a5. The process according to the above a1, wherein the liquid flow in the circumferential direction is imparted by a liquid supplied from the exterior of the decomposition reactor.

a6. The process according to the above a1 or a5, wherein the liquid supplied from the exterior of the decomposition reactor is the high boiling material supplied as raw material, or a return liquid of the liquid reaction residue discharged from the decomposition reactor.

b1. A process for producing (meth)acrylic acids, which is a process for producing acrylic acid, methacrylic acid or a (meth)acrylic ester by a reaction step comprising vapor-phase catalytic oxidation of propylene, propane or isobutylene, and, if necessary, further by a reaction step comprising an esterification step, characterized in that at the time when a high boiling mixture (hereinafter referred to as a high boiling material) containing a Michael addition product, is decomposed in a decomposition reactor to recover (meth)acrylic acids, a liquid reaction residue is intermittently discharged from the decomposition reactor.

b2. The process according to the above b1, wherein the discharge stop time is from 5 seconds to 5 minutes, and the discharge time is from 2 seconds to 5 minutes.

b3. The process according to the above b1 or b2, wherein the liquid high boiling material is continuously supplied to the decomposition reactor, and (meth)acrylic acids are continuously discharged from the vapor phase.

c1. In a process which comprises introducing a byproduct formed during production of (meth)acrylic acid and/or a byproduct formed during production of a (meth)acrylic ester into a reactor provided with a distillation column, thereby to thermally decompose the byproduct and at the same to carry out distillation for recovering a valuable substance, a method for decomposing the byproduct formed during production of (meth)acrylic acids, characterized in that as said distillation column, a distillation column which is internally provided with disk-and-donut type trays, is used.

c2. The process according to the above c1, wherein the byproduct formed during production of (meth)acrylic acid is the bottom liquid of a fractionating column in the final step for producing (meth)acrylic acid, and the byproduct formed during production of the (meth)acrylic ester is the bottom liquid of a fractionating column for separating a high boiling fraction in a purification step for the (meth)acrylic ester.

c3. The process according to the above c1 or c2, wherein the byproduct formed during production of (meth)acrylic acid and/or the byproduct formed during production of a (meth)acrylic ester contains a Michael addition product having water, an alcohol or (meth)acrylic acid added to a (meth)acryloyl group.

c4. The process according to any one of the above c1 to c3, wherein the thermal decomposition reaction temperature is from 120 to 280° C., and the thermal decomposition reaction time is from 0.5 to 50 hours.

d1. A process for decomposing a byproduct formed during production of (meth)acrylic acids, which comprises decomposing in a decomposition reactor a byproduct formed during production of (meth)acrylic acid and/or a byproduct formed during production of a (meth)acrylic ester, and distilling the decomposed product from the decomposition reactor, characterized in that oxygen or an oxygen-containing gas is added to the distillate from the decomposition reactor.

d2. The process according to the above d1, wherein the byproduct formed during production of (meth)acrylic acid is the bottom liquid of a fractionating column in the final step for producing (meth)acrylic acid, and the byproduct formed during production of the (meth)acrylic ester is the bottom liquid of a fractionating column in the final step for producing the (meth)acrylic ester, or the bottoms of a separation column for (meth)acrylic acid.

d3. The process according to the above d1 or d2, wherein the byproduct to be decomposed, contains a Michael addition product.

d4. The process according to any one of the above d1 to d3, wherein the gas containing oxygen is air or oxygen diluted with an inert gas.

d5. The process according to any one of the above d1 to d4, wherein the gas containing oxygen is added to a discharge line for a distillate from the decomposition reactor, or to the top portion of the decomposition reactor.

e1. In a process for producing acrylic acid, which comprises contacting with a solvent an acrylic acid-containing gas obtained by catalytic oxidation of propane or propylene, to collect acrylic acid in the form of an acrylic acid-containing solution, and purifying acrylic acid by distillation of the obtained acrylic acid-containing solution, a method for recovering acrylic acid, characterized in that the bottoms obtained from the bottom of a fractionating column for acrylic acid, or a liquid obtained by heating and concentrating such bottoms, is supplied to a thermal decomposition reactor to decompose an oligomer of acrylic acid in the liquid, and the obtained acrylic acid is recovered in a purification step, wherein from the liquid to be supplied to the thermal decomposition reactor or from the liquid recovered from the thermal decomposition reactor, maleic acid contained in the liquid is precipitated and separated.

e2. The process according to the above e1, wherein the composition of the liquid to be supplied to the thermal decomposition reactor or the liquid recovered from the thermal decomposition reactor, is adjusted to become a solution comprising at least 70 wt % of acrylic acid, from 1.6 to 28 wt % of maleic acid and/or maleic anhydride and water having a molar ratio of:

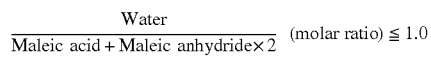

$$\frac{\text{Water}}{\text{Maleic acid} + \text{Maleic anhydride} \times 2} \text{ (molar ratio)} \leq 1.0$$

and maleic acid is precipitated at from 20 to 70° C. within a range of from 0.5 to 5 hours, followed by filtration and separation.

e3. The process according to the above e1 or e2, wherein at the time of the separation operation of maleic acid, an aliphatic or aromatic hydrocarbon is added in a volume ratio of from ½ to 4 times.

e4. The process according to the above e3, wherein the hydrocarbon to be added, is a solvent to be used for collecting the acrylic acid-containing gas, or an azeotropic agent to be used for dehydration distillation purification of acrylic acid.

f1. A method for installing a liquid level meter in a case where a liquid level meter is installed at a place where a liquid containing an easily polymerizable compound is stored, in an installation for production of the easily polymerizable compound, characterized in that a high pressure side detection line of the liquid level meter is connected to a discharge line for the liquid stored.

f2. The method according to the above f1, wherein the connection angle α between the high pressure side detection line and the liquid discharge line is from 5 to 90°.

f3. The method according to the above f1, wherein the dimensional ratio $D_2/D_1$ is from 1 to 20 where $D_1$ is the pipe diameter of the high pressure side detection line and $D_2$ is the pipe diameter of the liquid discharge line.

f4. The method according to the above f1, wherein the liquid discharge line is connected to a distillation column, a reflux tank of the distillation column, a decomposition reaction column, a thin film evaporator, a column top gas condensed liquid tank, a vertical storage tank, a horizontal storage tank or a tank.

f5. The method according to any one of the above f1 to f4, wherein the high pressure side detection line and/or the low pressure side detection line of the liquid level meter, is heated or warmed.

f6. The method according to any one of the above f1 to f5, wherein the high pressure side detection line and/or the low pressure side detection line of the liquid level meter, is connected with an inlet for a gas and/or a liquid.

f7. The method according to any one of the above f1 to f6, wherein the easily polymerizable compound is (meth)acrylic acid or its ester, and the liquid to be measured by the liquid level meter, contains at least one member selected from an acrylic acid dimer, β-(meth)acryloxypropionic acid esters, β-alkoxypropionic acid esters, β-hydroxypropionic acid and β-hydroxypropionic acid esters.

EXPLANATION OF REFERENCE SYMBOLS

Figure 1:
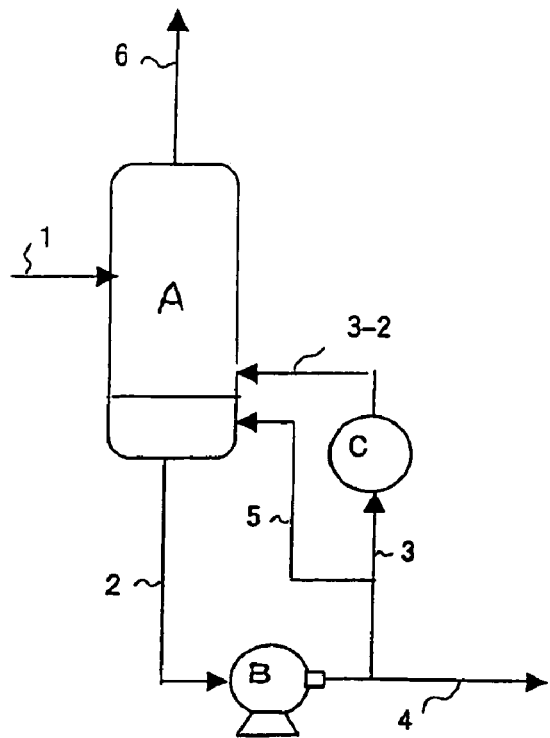
FIG. 1 shows an example of the production line by the thermal decomposition reaction (the spiral flow is formed by a return liquid to the decomposition reactor).

A: Decomposition reactor B: Bottom pump
C: Heat exchanger for heating D: Stirring means
E: Deposition F: Intermittent discharge control valve
1: High boiling material supply line
2: Bottom liquid discharge line
2-1, 2-2: Residual liquid discharge lines
3: Supply line for heat exchanger for heating
3-2: Return line for heating
4: Reaction residue discharge line
5: Spiral flow-forming return line
6: Valuable substance recovery line
7: Heating medium supply line
8: Heating medium discharge line
31, 33: Distillation columns
31D, 33D: Bottoms discharge ports
32A, 34A: Disk trays 32B, 34B: Doughnut trays
35: Distributor
41: Decomposition reaction column 42,46: Pumps
43: Heat exchanger for heating
44a: Column top gas line
44, 47: Heat exchangers 45: Cooled liquid tank
6A: (High boiling material) decomposition reaction column
6E: Column top gas-cooled liquid tank
$H_1$, $H_2$: Liquid level meters
62: Bottom liquid. discharge line
62a: Bottom liquid discharge short pipe
62b: Bottom liquid discharge conduit
65: Bottom liquid discharge line
65a: Bottom liquid discharge short pipe
65b: Bottom liquid discharge conduit
11, 13: High pressure side detection line
11a, 13a: High pressure side detection short pipes
11b, 13b: High pressure side detection conduits
12, 14: Low pressure side detection line
12a, 14a: Low pressure side detection short pipe
12b, 14b: Low pressure side detection conduits
α: Connection angle between high pressure side detection line and liquid discharge line

BEST MODE FOR CARRYING OUT THE INVENTION

Embodiment a

This Embodiment a has been accomplished on the basis of a discovery that in a decomposition reaction of a Michael addition product of acrylic acid or an acrylic ester, it is very effective to make the liquid flow at the column bottom in the circumferential direction in order to prevent accumulation of a solid substance at the bottom of the decomposition reaction column and thereby to avoid polymerization due to such accumulation.

1. (meth)acrylic acid and (meth)acrylic ester

The present invention can be applied to decomposition treatment of a high boiling mixture (high boiling material) obtained during production of (meth)acrylic acid or a (meth)acrylic ester. For example, it can be applied to a process for producing (meth)acrylic acid by vapor phase catalytic oxidation of propylene or isobutylene in the presence of a Mo—Bi type composite oxide catalyst to form acrolein or methacrolein, followed by vapor phase catalytic oxidation in the presence of a Mo—V type composite oxide catalyst. In such a case, the preliminary reaction to form mainly acrolein or methacrolein by oxidizing propylene or the like and the later reaction to form mainly (meth)acrylic acid by oxidizing acrolein or methacrolein, may be carried out in separate reactors, respectively, or such reactions may be carried out in one reactor packed with both the catalyst for the preliminary reaction and the catalyst for the later reaction. Further, the present invention is also applicable to a process for producing acrylic acid by vapor phase oxidation of propane by means of a Mo—V—Te type composite oxide catalyst or a Mo—V—Sb type composite oxide catalyst. Further, it is also applicable to a process for producing an acrylic ester by reacting an alcohol to (meth)acrylic acid.

A high boiling mixture (high boiling material) obtained after separating the desired product in these processes, is the object to be decomposed by the present invention. As the acrylic ester, a $C_{1-8}$ alkyl or cycloalkyl ester may be mentioned. For example, methyl acrylate, ethyl acrylate, butyl acrylate, isobutyl acrylate, tert-butyl acrylate, 2-ethylhexyl acrylate, 2-hydroxyethyl acrylate, 2-hydroxypropyl acrylate or methoxyethyl acrylate may be mentioned. Also with respect to a methacrylic ester, esters similar to the above may be mentioned.

Michael Addition Product

The Michael addition product contained in the high boiling material as the object to be decomposed by the present invention, is one having an active hydrogen compound such as water, an alcohol or (meth)acrylic acid ion-added to a carbon-carbon double bond of (meth)acrylic acid or a (meth)acrylic ester. Specifically, the Michael addition product in the case of producing acrylic acid, may, for example, be an acrylic acid dimer (hereinafter the dimer), an acrylic acid trimer (hereinafter the trimer), an acrylic acid tetramer (hereinafter the tetramer) or β-hydroxypropionic acid, as illustrated below.

Dimer: $H_2C=CH—C(=O)—O—CH_2—CH_2—C(=O)—OH$

Trimer: $H_2C=CH—C(=O)—O—CH_2—CH_2—C(=O)—O—CH_2—CH_2—C(=O)—OH$

Tetramer: $H_2C=CH—C(=O)—O—CH_2—CH_2—C(=O)—O—CH_2—CH_2—C(=O)—O—CH_2—CH_2—C(=O)—OH$ β-hydroxypropionic acid: $HO—CH_2—CH_2—C(=O)—OH$ On the other hand, the Michael addition product in the case of producing an acrylic ester, may, for example, be a Michael addition product of acrylic acid to the above acrylic ester, specifically a β-acryloxypropionic ester (an ester of the dimer); a Michael addition product of an alcohol, specifically an ester of the dimer, the trimer or the tetramer, β-hydroxypropionic acid, a β-hydroxypropionic esters or a β-alkoxypropionic esters.

β-acryloxypropionic ester: $H_2C=CH—C(=O)—O—CH_2—CH_2—C(=O)—OR$

β-alkoxypropionic ester: $RO—CH_2—CH_2—C(=O)—OR$

Ester of the trimer: $H_2C=CH—C(=O)—O—CH_2—CH_2—C(=O)—O—CH_2—CH_2—C(=O)—OR$

β-hydroxypropionic ester: $HO—CH_2—CH_2—C(=O)—OR$

β-hydroxypropionic acid: $HO—CH_2—CH_2—C(=O)—OH$

Also with respect to methacrylic acid and a methacrylic ester, substantially the same as the above will apply. Only the difference is that as a result of substitution of hydrogen at the α-position for a methyl group, propionic acid (ester) becomes isobutyric acid (ester).

The high boiling material to be supplied to the decomposition reactor is a high boiling mixture containing the above Michael addition product. The content of the Michael addition product may vary to a large extent by the production process. However, it is common to employ a high boiling material containing a Michael addition product in an amount of from 1 to 90 wt %, preferably from 2 to 70 wt %. The high boiling material also contains a compound by-produced in the step of producing (meth)acrylic acids or a material to be used as an assisting agent in the process. Specifically, (meth)acrylic acid, (meth)acrylic esters, maleic acid, maleic acid esters, furfural, benzaldehyde, polymers, oligomers, alcohols to be used as materials for producing esters, or polymerization inhibitors, specifically, copper acrylate, copper dithiocarbamate, a phenol compound or a phenothiazine compound, may, for example, be mentioned.

The copper dithiocarbamate may, for example, be a copper dialkyldithiocarbamate such as copper dimethyldithiocarbamate, copper diethyldithiocarbamate, copper dipropyldithiocarbamate or copper dibutyldithiocarbamate, a copper cyclic alkylenedithiocarbamate such as copper ethylenedithiocarbamate, copper tetramethylenedithiocarbamate, copper pentamethylenedithiocarbamate or copper hexamethylenedithiocarbamate, or a copper cyclic oxydialkylenedithiocarbamate such as copper oxydiethylenedithiocarbamate.

The phenol compound may, for example, be hydroquinone, methoxyhydroquinone (methoquinone), pyrogallol, resorcinol, phenol or cresol. The phenothiazine compound may, for example, be phenothiazine, bis-(α-methylbenzyl)phenothiazine, 3,7-dioctylphenothiazine or bis(α-dimethylbenzyl)phenothiazine. In some cases, materials other than the above-mentioned may be contained depending upon the process, without adversely affecting the present invention.

Process for Producing (meth)acrylic acids

The above-mentioned high boiling material may, for example, be obtained via a purification step such as extraction or distillation after contacting a (meth)acrylic acid-containing gas obtained by vapor phase catalytic oxidation of propylene or acrolein, with water or an organic solvent to collect (meth)acrylic acid in the form of a solution. The process for producing a (meth)acrylic ester, for example, comprises an esterification reaction step of reacting (meth)acrylic acid with an alcohol in the presence of an organic acid or a cationic ion exchange resin or the like, as a catalyst, and a purification step of carrying out extraction, evaporation or distillation as a unit operation to concentrate the crude (meth)acrylic ester solution obtained by the reaction. Each unit operation is suitably selected depending upon the raw material ratio of (meth)acrylic acid to the alcohol in the esterification reaction, the type of the catalyst to be used for the esterification reaction or the physical properties of the raw materials, reaction byproducts, etc.

Flowchart for the Thermal Decomposition Reaction of the High Boiling Material

The description will be made with reference to the drawings. FIG. 1 is an example of the production line by the thermal decomposition reaction of the present invention. The high boiling material is supplied via a line 1 to a decomposition reactor A. The supply to the decomposition reactor A may be carried out continuously or intermittently (semi-continuously), but continuous supply is preferred. A valuable substance formed in the decomposition reactor and a part of materials constituting the high boiling material will be continuously withdrawn in a gas state from the recovery line 6 and will be returned to the production process, as it is in the gas state or as cooled in a liquid state. In a case where the decomposition reactor A is a column type reactor, a part of the cooled liquid may be returned as a reflux liquid to the top of the decomposition reactor.

The residual liquid will be withdrawn via a residual liquid discharge line 2 and the bottom pump B, and a part thereof is supplied to a heat exchanger C for heating via a line 3 and returned to the decomposition reactor A. The rest will be discharged out of the system via a line 4. The relation between the return liquid amount and the discharge amount may suitably be set depending upon various factors such as the heat balance at the heat exchanger for heating and the retention time at the decomposition reactor. The flow in the circumferential direction (hereinafter sometimes referred to as a spiral flow) in the decomposition reactor of the present invention is formed by the return liquid of the line 5 in FIG. 1. The line 5 is disposed in the tangent direction of the main body of the decomposition reactor, and the spiral flow will be formed in the reactor by the flow of the liquid supplied from the line 5. The return liquid amount of the line 5 is usually selected within a range of from 0.2 to 5 times by weight, based on the amount of the raw material supplied from the line 1. If the return liquid amount is less than the above range, an adequate spiral flow tends to be hardly formed. The return liquid for heating, flowing through the line 3-2, is not related to formation of the spiral flow, and its flow rate is determined depending upon e.g. a heat balance.

Figure 2:
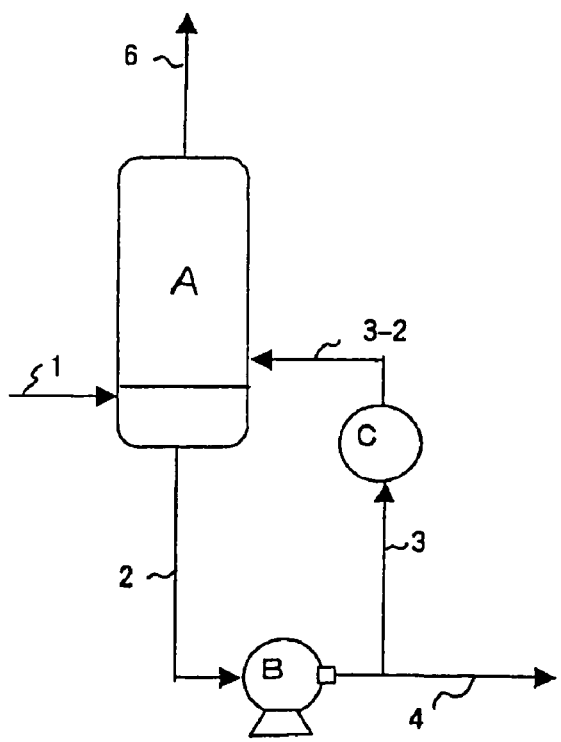
FIG. 2 shows an example of the production line by the thermal decomposition reaction (the spiral flow is formed by the raw material liquid supplied to the decomposition reactor).

FIG. 2 is one wherein the flow in the circumferential direction is made by the raw material liquid supplied to the decomposition reactor, and such is carried out by the line 1. The line 1 is disposed in a tangent direction of the main body of the decomposition reactor, and the spiral flow will be formed in the reactor by the raw material liquid supplied from the line 1. In this case, the line 1 is required to be controlled so that the liquid surface will be below the liquid surface of the reaction liquid retained in the decomposition reactor.

Figure 3:
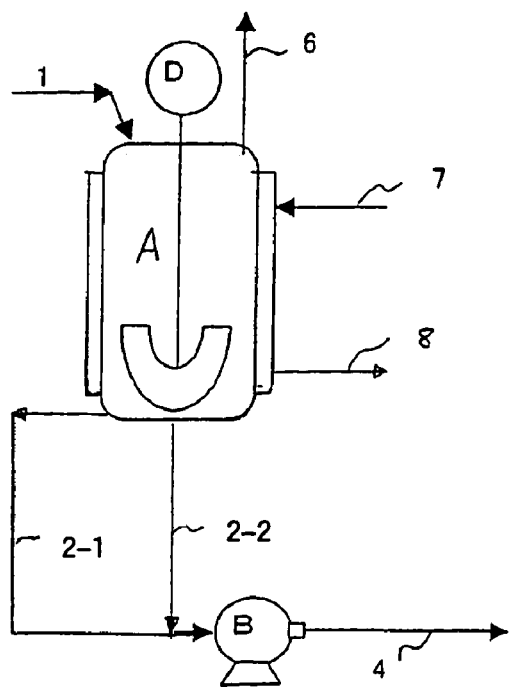
FIG. 3 shows an example of the production line by the thermal decomposition reaction (the spiral flow is formed by stirring vanes).

FIG. 3 is an example of an apparatus to form the spiral flow in the decomposition reactor by means of stirring vanes.

The high boiling material is supplied from the line 1 to the decomposition reactor A. a valuable substance and a part of materials constituting the high boiling material, decomposed in the decomposition reactor A will be withdrawn from a recovery line 6 and will be returned to the production process in a gas state or as cooled in a liquid state. In a case where the decomposition reactor A is a column type reactor, the part of cooled liquid may be returned as a reflux liquid to the top of the decomposition reactor. The residual liquid will be discharged from the line 4 out of the system. The heat medium supply line 7 and the heat medium discharge line 8 are exemplary, and depending upon the type of the heat medium, the positions of the supply line and the discharge line may be changed.

The flow in the circumferential direction (the spiral flow) in the decomposition reactor of the present invention is carried out by the residual liquid-stirring means D in FIG. 3. The stirring means D comprises stirring vanes, a stirring shaft and a motor for stirring, whereby the internal liquid of the decomposition reactor is capable of forming a liquid flow in the circumferential direction. The rotational speed of the stirring vanes is usually suitably selected depending upon the shape or the diameter of the vanes, so that the forward end speed of the vanes will be usually from 0.2 to 5 m/sec. The residual liquid forming the spiral flow will be withdrawn from the residual liquid discharge line 2-1 or 2-2. The residual liquid discharge line 2-1 represents an example wherein it is disposed in a tangent direction of the main body of the decomposition reactor, and the residual liquid discharge line 2-2 represents an example wherein it is disposed at the center portion of the decomposition reactor. In the case of the discharge line 2-1, together with the stirring effect of the vanes, a good spiral flow may be maintained.

Figure 4:
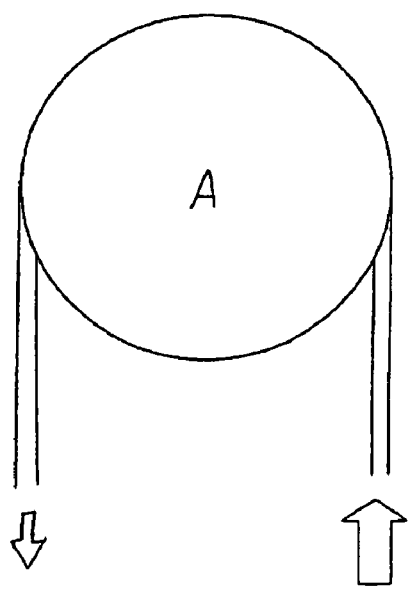
FIG. 4 is a view showing the cross section in a horizontal direction of the decomposition reactor A and the positional relation for connection with the lines for forming the spiral flow.

FIG. 4 is a view showing the cross section of the decomposition reactor A and the positional relation of connection with the spiral flow-forming lines. The line 5 (spiral flow-forming return line 5) in FIG. 1 or the line 1 (high boiling material-supply line 1) in FIG. 2, is disposed in a tangent direction of the main body of the decomposition reactor, whereby a flow in the circumferential direction (a spiral flow) can be formed within the decomposition reactor. Further, the residual liquid discharge line 2-1 in FIG. 3 is disposed in a tangent direction of the main body of the decomposition reactor, whereby together with the stirring effect of vanes, a good spiral flow can be maintained.

Figure 5:
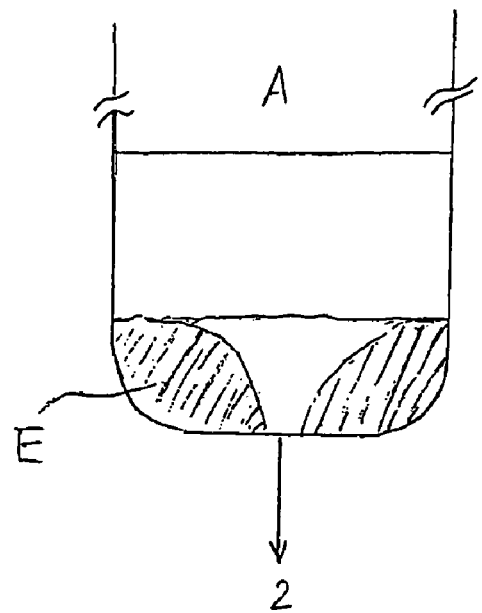
FIG. 5 is a view schematically showing a solid substance accumulated at the bottom of the decomposition reactor A (a cross-sectional view in the longitudinal direction of the column).

FIG. 5 is a view (column longitudinal cross-sectional view) schematically showing a solid substance accumulated at the bottom of the decomposition reactor A. If the left and right accumulated products are joined, the discharge port will be in a clogged state, whereby withdrawal of the bottom liquid will be impossible, and the bottom pump B may undergo cavitation.

Decomposition Reaction of the High Boiling Material

The Michael addition product contained in the high boiling material can be decomposed to a monomer containing (meth)acrylic acid as the main component. In a case where a (meth)acrylic ester is contained in the high boiling material, it may be hydrolyzed to (meth)acrylic acid and an alcohol, or may be recovered as it is in the form of an ester without decomposition, depending upon the conditions.

The temperature for the decomposition reaction is adjusted to from 110 to 250° C., preferably from 120 to 230° C. In FIG. 1, the high boiling material is heated in the heat exchanger C for heating, and the temperature is controlled. Other than the one where a heater is installed outside the decomposition reactor A, as shown in FIG. 1, an inner coil type heater installed in the decomposition reactor or a jacket type heater installed around the decomposition reactor, is, for example, available, and a heating device of any type may be used.

The retention time for the decomposition reaction varies depending upon the composition of the high boiling material, the presence or absence of the catalyst and the decomposition reaction temperature. In a case where the decomposition reaction temperature is low, it is a relatively long time, such as from 10 to 50 hours, and in a case where the decomposition reaction temperature is high, it is from 30 minutes to 10 hours. The reaction pressure may be either under a reduced pressure condition or under an atmospheric pressure condition.

The decomposition reaction can be carried out by using only the high boiling material as the object. However, for the purpose of accelerating the decomposition reaction, it may be carried out in the presence of an acid catalyst or in the presence of water. As the catalyst for the decomposition reaction, an acid or a Lewis acid, such as sulfuric acid, phosphoric acid, methanesulfonic acid, paratoluenesulfonic acid or aluminum chloride, is mainly used. The catalyst and/or water may preliminarily be mixed with the high boiling material, or may be supplied to the decomposition reactor A separately from the high boiling material. In a case where a polymer, a polymerization inhibitor, a catalyst, etc. are contained in the high boiling material, they will usually remain and be concentrated in the decomposition residue without being decomposed.

Structure of the Decomposition Reactor

The structure of the decomposition reactor A may be any structure such as a column type or a tank type. In the case of a column type reactor, trays or packing materials which are commonly used in a distillation column, may be installed as a content, whereby not only the decomposition reaction but also a distillation operation can be carried out, such being preferred. As the packing material, a regular packing material such as SULZER PACKING manufactured by SULZER BROTHERS LTD., SUMITOMO SULZER PACKING or MELLAPACK manufactured by SUMITOMO HEAVY INDUSTRIES, LTD., GEMPAK manufactured by GLITSCH, MONTZ PACK manufactured by MONTZ, GOODROLL PACKING manufactured by TOKYO TOKUSHU KANAAMI K.K., HONEYCOMB PACKING manufactured by NGK INSULATORS, LTD. or IMPULSE PACKING manufactured by NAGAOKA INTERNATIONAL CORPORATION, may, for example, be used.

As an irregular packing material, INTALOX SADDLE manufactured by NORTON, TELLERETTE manufactured by Nittetu Chemical Engineering Ltd., PALL RING manufactured by BASF, CASCADE MINI-RING manufactured by MASS TRANSFER or FLEXIRING manufactured by JGC CORPORATION, may, for example, be mentioned. Any one of such packing materials may be used, or more than one of them may be used in combination.

The trays may, for example, be bubble cap trays, perforated plate trays, bubble trays, superflux trays or max flux trays having a downcomer or dual trays or disk and doughnut type trays having no downcomer. The trays or the packing materials may be used in combination, or no such content may be present in the decomposition reactor.

In the present invention, the liquid flow in the circumferential direction (the spiral flow) is one which is generated forcibly, and such can be carried out by supplying the high boiling material or the return liquid of bottoms (the bottom liquid) from a tangent direction of the reactor. In a case where a supply inlet from a tangent direction is not present, the spiral flow is formed by stirring vanes provided in the reactor. In some cases, both means may be used in combination.

In the case of a tank type reactor provided with stirring vanes, a baffle may be provided, as the case requires. The stirring vanes may be of any type so long as they are capable of generating a circumferential flow. Specifically, anchor vanes, (at least one stage) multistage paddle vanes, (at least one stage) multistage inclined paddle vanes, lattice vanes, MAXBLEND vanes (tradename, manufactured by SUMITOMO HEAVY INDUSTRIES, LTD.), FULLZONE VANES (tradename, manufactured by SHINKO PANTEC CO., LTD., etc. may be mentioned, and at least one type may be used in at least one stage. FULLZONE VANES are such that radial flow type vanes are attached in two stages in a rotation axis direction on a rotational shaft installed vertically at the center of the reactor, and vanes adjacent in the rotational axis direction are in a positional relation to the rotational axis direction such that their phases are displaced from each other by not more than 90°, and the lowest portion of the upper stage one of the vanes adjacent in the rotational axis direction, is located below the highest portion of the lower stage one (see JP-A-7-33804). Particularly preferred as stirring vanes, are anchor vanes, lattice vanes or FULLZONE VANES.

With respect to baffle plates (hereinafter baffles) installed together with stirring vanes, there is no restriction in the present invention. Any type may be employed, or no baffles may be installed. Specifically, a rod type, a plate type, a comb type may, for example, be mentioned, and at least one type and at least one member may be installed. It is particularly preferred to install one rod type or one plate type.

Discharge of the Residue of the Decomposition Reactor

The decomposition residue may be discharged from the decomposition reactor by a suitable method. The bottom discharge position of the decomposition reactor may be at any place so long as it is the bottom end portion of the column. It is preferably within a range of ½ of the column diameter from the lowest portion of the bottom. If it is located above the end portion, a solid substance will be accumulated at the end portion. The residue is stored in e.g. a tank and then recycled to incineration treatment or a production process. On the other hand, acrylic acid, methacrylic acid, an alcohol, etc. as decomposition products of the Michael addition product or the ester will be continuously discharged from the top (the column top) of the decomposition reactor. They are led to a purification system or recycled to a suitable position in the production process.

Embodiment b

This Embodiment b has been accomplished on the basis of a discovery that the decomposition reaction of the Michael addition product of (meth)acrylic acids can be carried out without clogging for a long time, by pulse discharge i.e. intermittent discharge of the bottom liquid instead of continuous discharge from the bottom of the reactor. The reason as to why clogging can effectively be prevented, is not clearly understood. However, from the experimental facts, the present inventors consider that the clogging in a pipe under a constant flow, will be disturbed by the liquid flow by intermittent flowing, and due to the disturbing effect of the liquid flow, the clogging can extremely effectively be suppressed in spite of the fact that the liquid flow will be temporarily stopped.

"(Meth)acrylic acid and (meth)acrylic ester", "Michael addition product" and "Process for producing (meth)acrylic acids" are the same as in the case of Embodiment a.

Figure 6:
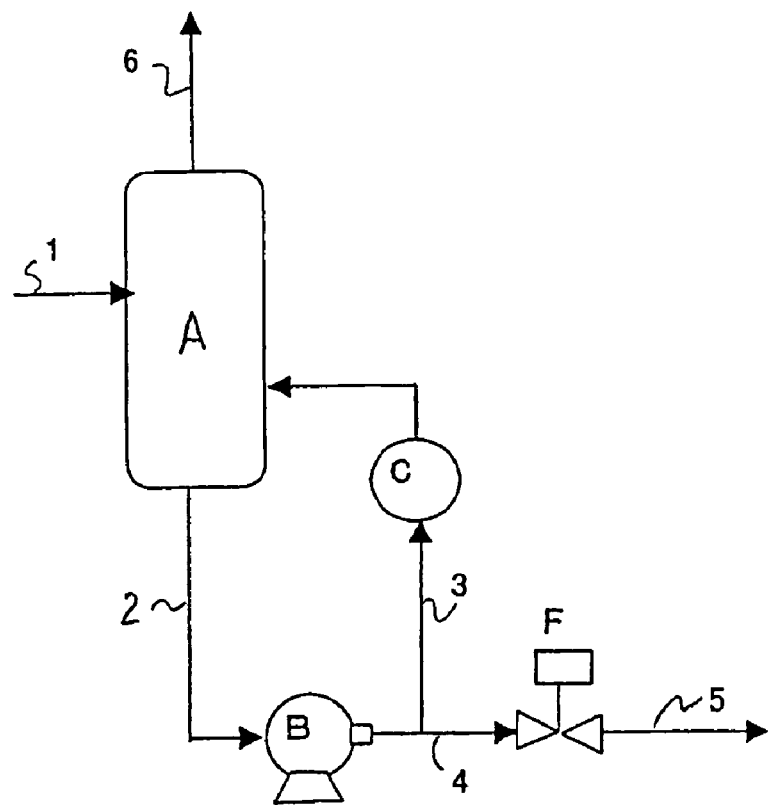
FIG. 6 shows an example of the production line by the thermal decomposition reaction.

Flowchart for the Production Line by Thermal Decomposition Reaction of the High Boiling Material FIG. 6 is an example of the production line by the thermal decomposition reaction of the present invention, which is the same as in the case of Embodiment a except that C represents a heat exchanger for heating, F an intermittent discharge control valve, and 3 a supply line for the heat exchanger for heating.

The high boiling material is supplied to a decomposition reactor A from a line 1. The supply to the decomposition reactor A may be carried out continuously or intermittently (semicontinuously), but continuous supply is preferred. A valuable substance and a part of materials constituting the high boiling material, formed in the decomposition reactor is continuously withdrawn in a gas state from a recovery line 6 and returned to the production process, as it is in a gas state or as cooled in a liquid state. In a case where the decomposition reactor A is a column type reactor, a part of the cooled liquid may be returned as a reflux liquid to the top of the decomposition reaction column. The bottom liquid is withdrawn from the line 2, and via a pump B, a part is supplied to a heat exchanger C for heating and returned to the decomposition reactor A. The rest will be discharged out of the system from the line 4 via an intermittent discharge control valve D as the gist of the present invention. Reference numeral 5 represents a transport pipe to a storage tank.

"Decomposition reaction of the high boiling material" and "Structure of the decomposition reactor" are the same as in the case of Embodiment a.

Intermittent Discharge

In Embodiment b, the most significant feature is that the decomposition residue is intermittently discharged from the decomposition reactor. The intermittent discharge is carried out by an intermittent discharge control valve D. The closing time of the valve D is usually from 5 seconds to 5 minutes, preferably from 10 seconds to 2 minutes, and the opening time of the valve D is usually from 2 seconds to 5 minutes, preferably from 3 seconds to 2 minutes. The opening ratio of the control valve D (percentage of opening time/(opening time+closing time)) is preferably within a range of from 2 to 50%, more preferably from 5 to 30%. If the closing time is shorter and the opening time is longer than the above range, the clogging suppression effect may not sufficiently be obtained due to an inertia of the flow of the decomposition residue. If the closing time is long and the opening time is short, clogging of the pipeline is likely to take place due to an influence of the static state of the liquid in the piping, such being undesirable. In the continuous discharge (opening rate: 100%), clogging of the pipe will take place as is evident also from a Comparative Example hereinafter.

On the other hand, acrylic acid, methacrylic acid, an alcohol, etc. as decomposition products of the Michael addition product or the ester, will be continuously discharged from the top of the decomposition reactor (column top). They will be led to a purification system, or may be recycled to an appropriate position of the production process.

Embodiment c

In Embodiment c, as trays for the distillation column, disk and doughnut type trays are used, whereby problems of adhesion, deposition and accumulation of the solid substance have been solved. Namely, disk and doughnut type trays are such that disk trays and doughnut trays are alternately installed with a suitable distance, and as shown in FIGS. 7 and 8, the structure is very simple, and the opening is extremely large, whereby a solid substance is hardly precipitated or accumulated, whereby it is possible to solve the problems of adhesion, deposition and accumulation of the solid substance.

Accordingly, by using a distillation column equipped with disk and doughnut type trays, decomposition of the byproduct and recovery of a valuable substance during the production of (meth)acrylic acids, can be carried out constantly. The disk and doughnut type trays have a structure which is extremely simple. Accordingly, as compared with a distillation column employing conventional trays or packing material, there is a merit such that the production cost of the distillation column and construction costs such as installation costs, can be very low.

Now, a practical embodiment of the method for decomposing the byproduct formed during production of (meth) acrylic acids according to Embodiment c will be described in detail. Firstly, with reference to FIGS. 7 and 8, the construction of a distillation column equipped with disk and doughnut type trays suitable for Embodiment c will be described. FIG. 7(*a*) is a schematic cross-sectional view showing a distillation column equipped with flat plate type disks and doughnuts, and FIG. 7(*b*) is an enlarged perspective view of the essential portions of FIG. 7(*a*). Further, FIG. 8(*a*) is a schematic cross-sectional view showing a distillation column equipped with sloping plate type disk-and-doughnut trays, and FIG. 8(*b*) is an enlarged view of the essential portions of FIG. 8(*a*).

Figure 7:
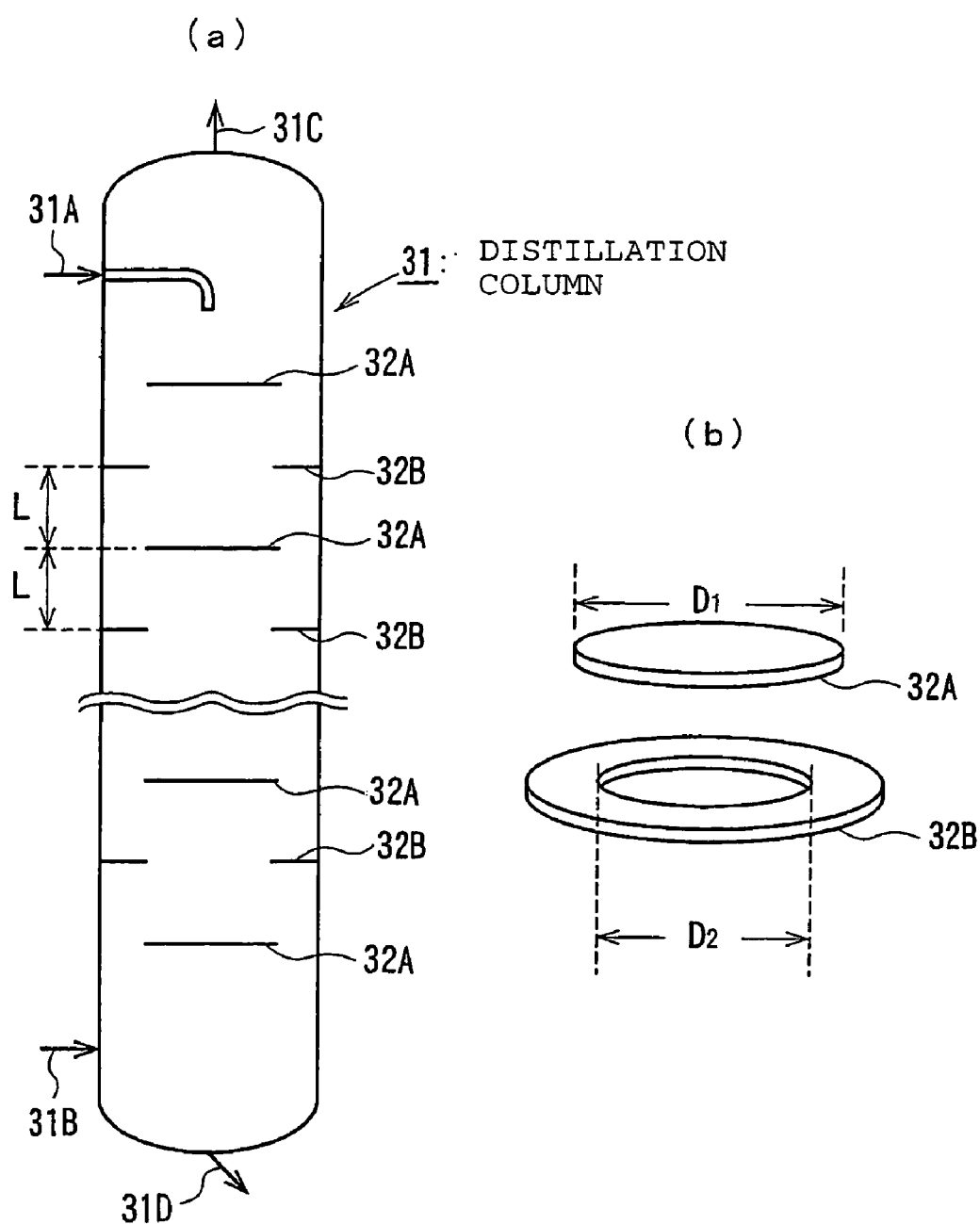
FIG. 7(a) is a schematic cross-sectional view showing a distillation column provided with flat plate disks and doughnuts, suitable for carrying out the method for decomposing a byproduct formed during the production of (meth)acrylic acids according to the present invention.
FIG. 7(b) is an enlarged perspective view of the essential portions of FIG. 7(a).
Figure 8:
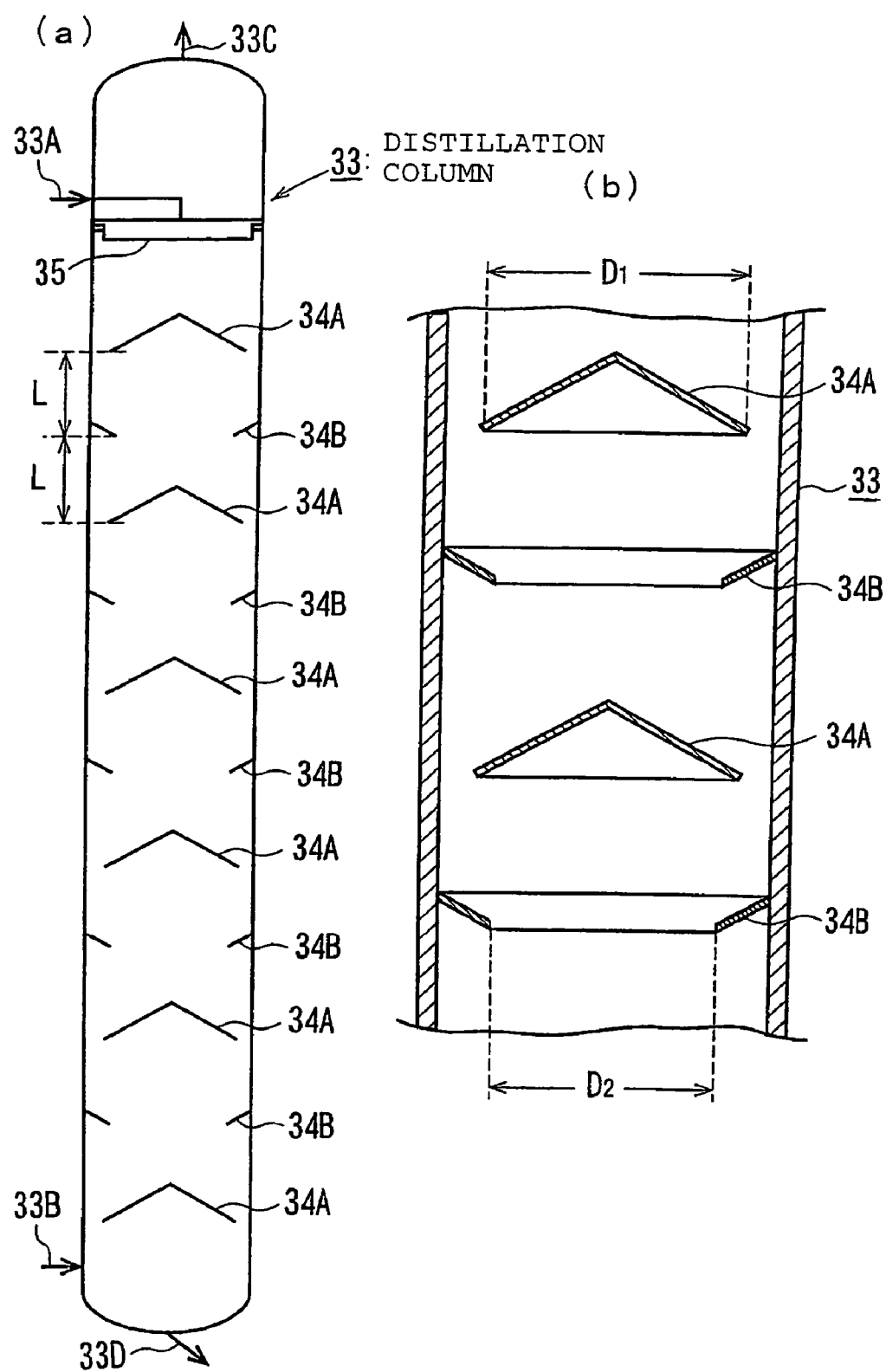
FIG. 8(a) is a schematic cross-sectional view showing a distillation column provided with slanted plate disks and doughnuts, suitable for carrying out the method for decomposing a byproduct formed during the production of (meth)acrylic acids according to the present invention.
FIG. 8(b) is an enlarged view of the essential portions of FIG. 8(a).
Figure 9:
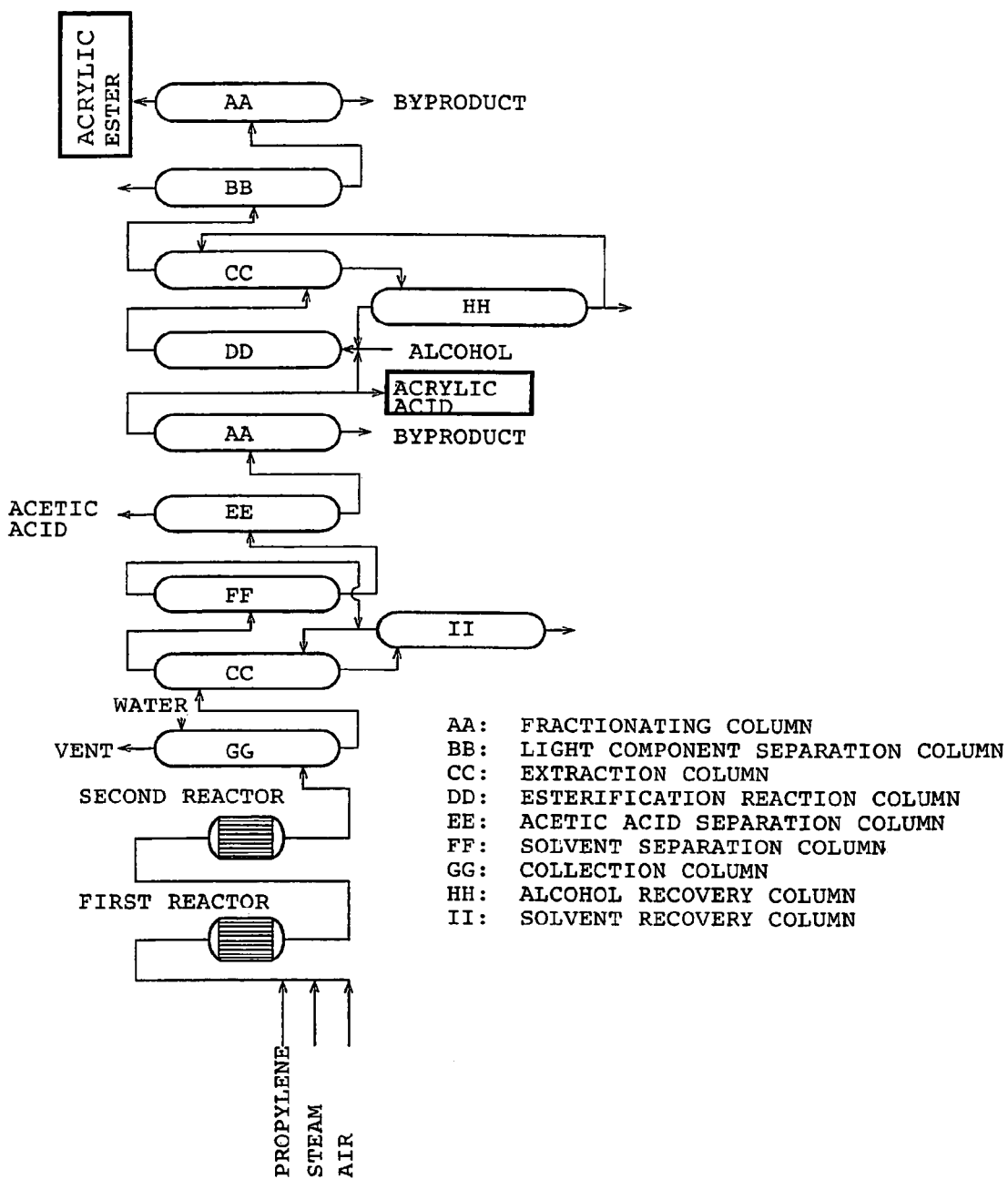
FIG. 9 is an example of the flowchart for production of acrylic acid and an acrylic ester.
Figure 10:
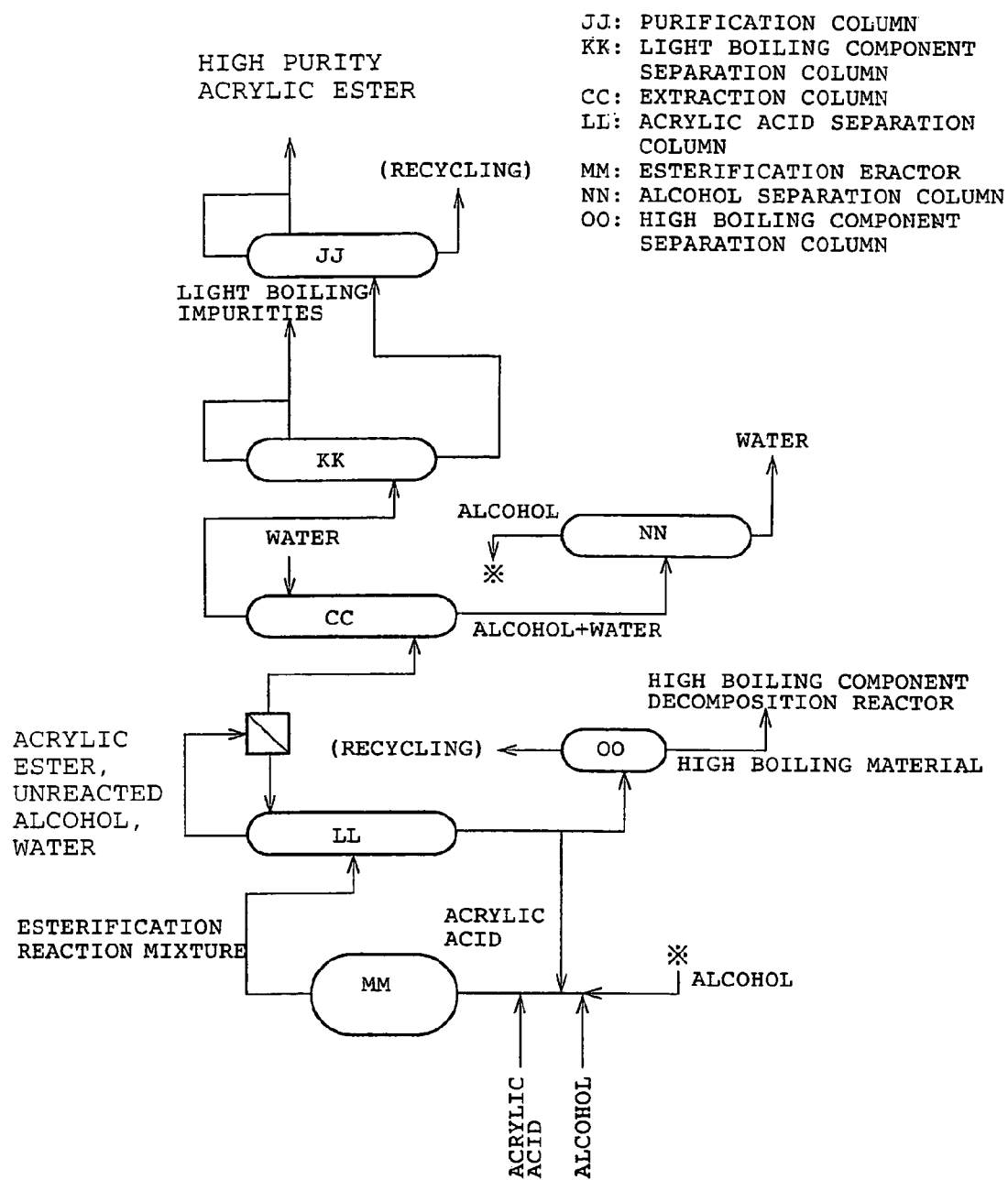
FIG. 10 is another example of the flowchart for production of an acrylic ester.

The disk-and-doughnut type trays are such that a plurality of disk-shaped trays and doughnut-shaped trays are alternately disposed with a suitable distance in the distillation column, and in distillation column 31 in FIG. 7, flat plate type disk-shaped trays 32A and doughnut-shaped trays 32B are alternately disposed in the column. Whereas, in the distillation column 3 in FIG. 8, sloping plate type disk-shaped trays 34A and doughnut-shaped trays 34B slanted in the liquid flow direction, are alternately disposed. In the distillation columns 31 and 33 in FIGS. 7 and 8, 31A and 33A are liquid inlets, and 31B and 33B are vapor inlets. Further, 31C and 33C are vapor outlets, and 31D and 33D are bottom liquid outlets. 35 in FIG. 8 is a distributor (dispersing device).

The distance between the disk-shaped trays 32A and 34A and the doughnut-shaped trays 32B and 34B (L in FIGS. 7 and 8) is preferably at least 250 mm in order to suppress entrainment. If this distance L is excessively large, the height of the distillation column will have to be increased, and therefore, it is preferably at most 500 mm.

The plan view-shape of the disk-shaped tray 32A or 34A is preferably a perfect circle, and its center is preferably located at the center of the distillation column. Likewise, the plan view-shape of the doughnut-shaped tray 32B or 34B is preferably a perfect circular ring, and the outer periphery of the doughnut-shaped tray 32B or 34B is preferably closely in contact with the inner wall of the distillation column 31 or 33.

The diameter of the disk-shaped tray 32A or 34A ($D_1$ in FIGS. 7 and 8) and the diameter of the opening of the doughnut-shaped tray 32B or 34B ($D_2$ in FIGS. 7 and 8) (hereinafter sometimes referred to as "inner diameter") are suitable selected within a range of from 55 to 74% of the inner diameter of the distillation column 31 or 33. This size corresponds to a range of from 30 to 55% as represented by the open area ratio in the distillation column 31 or 33.

In order to avoid short path (short circuit) of the down flow of the liquid in the distillation column 31 or 33, the diameter $D_1$ of the disk-shaped tray 32A or 34A is preferably slightly larger than the inner diameter $D_2$ of the doughnut-shaped tray 32B or 34B.

With respect to the shape of trays, simple flat plate type trays 32A and 32B as shown in FIG. 7 are preferred. However, as shown in FIG. 8, with trays 34A and 34B slightly slanted to the liquid flow direction, it is possible to further suppress accumulation of a solid substance. The sloping angle in such a case is not particularly limited, but it is usually preferably set within a range of from 5 to 45° against a horizontal direction.

A method of installing the disk-shaped trays 32A and 34A and the doughnut-shaped trays 32B and 34B in the distillation columns 31 and 33 may be any method. It may, for example, be a method of fixing them by means of supports extended from the walls of the distillation columns, a method of welding them to the walls of the distillation column, or a method wherein the respective disk-shaped trays and doughnut-shaped trays are entirely fixed to a vertical support and mounted in the distillation columns in the form of an integral structure.

The number of plates of the disk-shaped trays and doughnut-shaped trays to be installed in the distillation column is not particularly limited and is suitably selected so that the separation performance required for the particular process, can be obtained. If the plate number is too small, the distillation amount of the high boiling component tends to be large, and the recycling amount will increase, and the treating ability of the decomposition reactor will decrease, such being undesirable. On the other hand, if the plate number is increased more than necessary, not only the construction costs will increase, but also the distillation concentration, at the top, of the polymerization inhibitor contained in the raw material liquid decreases, whereby an undesirable polymerization reaction of the distillate is likely to take place, such being undesirable. Accordingly, the disk-shaped trays and doughnut-shaped trays to be installed, are preferably selected within a range of from 5 to 20 plates (for this plate number, one disk-shaped tray or doughnut-shaped tray will be taken as one plate).

(Meth)acrylic acid in Embodiment c is preferably one obtained by a catalytic vapor phase oxidation reaction of propane, propylene, acrolein, isobutylene, t-butyl alcohol or the like, and a gaseous oxidation reaction product is rapidly cooled and quenched with water. Then, separation of water and (meth)acrylic acid is carried out by an azeotropic distillation method employing an azeotropic solvent or by an extraction method employing a solvent. Further, low boiling compounds such as acetic acid are separated, and then a heavy component such as the Michael addition product is separated to obtain high purity (meth)acrylic acid. Otherwise, water and acetic acid may be separated simultaneously by means of an azeotropic agent. The above-mentioned Michael addition product will be concentrated in the high boiling fraction, and it is preferred that this fraction, i.e. usually the bottom liquid of a fractionating column, is mixed with the byproduct formed during production of a (meth)acrylic ester, so that they are treated all together.

The (meth)acrylic ester in Embodiment c is not particularly limited and may, for example, be methyl (meth)acrylate, ethyl (meth)acrylate, n-butyl (meth)acrylate, i-butyl (meth)acrylate, n-hexyl (meth)acrylate, 2-ethylhexyl (meth)acrylate, n-octyl (meth)acrylate, methoxyethyl (meth)acrylate, i-nonyl (meth)acrylate or i-decyl (meth)acrylate.

The Michael addition product is a byproduct to be formed in a reaction step or a purification step in the production of (meth)acrylic acid and a (meth)acrylic ester, and it is a compound having (meth)acrylic acid, acetic acid, an alcohol or water Michael-added at the α- or β-position of a compound having a (meth)acryloyl group present in such a production process. The compound having a (meth)acryloyl group present in the production process, may, for example, be (meth)acrolein, a (meth)acrylic acid, a carboxylic acid having a (meth)acryloyl group, such as a β-acryloxypropionic acid or a β-methacryloxyisobutyric acid (hereinafter both may generally be referred to as the dimer) having (meth)acrylic acid Michael added to such (meth)acrylic acid, a (meth)acrylic acid trimer (hereinafter the trimer) having (meth)acrylic acid Michael-added to such a dimer, or a (meth)acrylic acid tetramer (hereinafter the tetramer) having (meth)acrylic acid Michael-added to such a trimer, or the corresponding (meth)acrylic ester having such a carboxylic acid having a (meth)acryloyl group esterified with an alcohol. Further, likewise, one having (meth)acrylic acid Michael-added to (meth)acrolein may also be contained. Specifically, the Michael addition product of the present invention includes β-acryloxypropionic acid or β-methacryloxyisobutyric acid, and its ester and aldehyde compound (β-acryloxypropanal or β-methacryloxyisobutanal), a β-alkoxypropionic acid and its ester, β-hydroxypropionic acid or β-hydroxyisobutyric acid, and their esters and aldehyde compounds, as well as dimers, trimers, tetramers, etc., and their β-acryloxy compounds, β-acetoxy compounds, β-alkoxy compounds and β-hydroxy compounds. Further, a compound having acetic acid Michael-added to a (meth)acryloyl group, is present although it may be in a very small amount.

In Embodiment c, as a method for producing a (meth)acrylic ester, it is common to employ a method of reacting an alcohol to (meth)acrylic acid for esterification, or a method for producing an acrylic ester of a higher alcohol, by reacting an acrylic ester of a lower alcohol with a higher alcohol for transesterification. Further, the production process may be either a batch system or a continuous system. As a catalyst for such esterification or transesterification, an acid catalyst is usually employed.

The process for producing a (meth)acrylic ester preferably comprises the reaction step and a purification step for carrying out washing, extraction, evaporation, distillation or the like as a unit operation to carry out separation of the catalyst, concentration, purification, etc. of the crude (meth)acrylic ester obtained in such a reaction step. The starting material molar ratio of the (meth)acrylic acid or the (meth)acrylic ester to the alcohol in the reaction step may suitably be selected depending upon the type and amount of the catalyst to be used for the reaction, the reaction system, the reaction conditions, or the type of the alcohol used as the raw material.

The Michael addition product by-produced mainly by the reaction will be concentrated at the bottom of the distillation column (the fractionating column) to separate a high boiling fraction. Accordingly, in the present invention, this bottom liquid is, as the object to be treated, subjected to thermal decomposition together with the byproduct from the previous (meth)acrylic acid production step, and the obtained useful component will be recovered for the reaction step for (meth)acrylic ester or a purification step.

Here, the distillation column to separate the high boiling fraction may vary depending upon the type of the (meth)acrylic ester to be produced or the process to be used, but usually, it is one to separate (meth)acrylic acid and the high boiling fraction, or one to separate a (meth)acrylic ester and the high boiling fraction, or one to separate (meth)acrylic acid, an alcohol and a (meth)acrylic ester, and the high boiling fraction. The present invention can be applied to all of them.

In the bottom liquid of the high boiling fraction-separation column, the above-mentioned Michael addition product is concentrated, but in addition, substantial amounts of (meth)acrylic acid and/or a (meth)acrylic ester are contained, and further, high boiling components such as a polymerization inhibitor used in the process, an oligomer or polymer formed in the process, high boiling impurities in the raw material or their reaction products, are contained. Further, in some cases, the catalyst used for the esterification or transesterification step may be contained.

As mentioned above, the Michael addition product by-produced during the step for producing (meth)acrylic acid will usually be concentrated at the bottom of a distillation column (fractionating column) for separating the product of (meth)acrylic acid from the heavy fraction. In this bottom liquid, a substantial amount of (meth)acrylic acid is also contained, and further, the polymerization inhibitor used in the process, the oligomer formed in the process or high boiling components are also contained.

In Embodiment c, as the reactive distillation system wherein the decomposition reaction of the Michael addition product and distillation and recovery of the valuable substance are simultaneously carried out, any system such as a continuous system, a batch system, a semi-batch system or an intermittent discharge system may be employed, but a continuous system is preferred. Further, the type of the reactor may be any of a completely mixing type stirring tank reactor, a circulation type completely mixing tank reactor or a simple hollow reactor, without being restricted to any particular type.

As the catalyst, a known Lewis acid or Lewis base catalyst may be used, but simple thermal decomposition employing no catalyst may be used. As conditions for the decomposition reaction, the temperature is usually from 120 to 280° C., preferably from 140 to 240° C., and the liquid retention time based on the discharge liquid, is from 0.5 to 50 hours, preferably from 1 to 20 hours. With respect to the reaction pressure, a condition is preferably selected so that the majority of (meth)acrylic acid, the (meth)acrylic ester, the alcohol, etc. to be recovered, will be distilled at the reaction temperature.

In Embodiment c, a distillation column provided with disk-and-doughnut type trays as shown in FIG. 7 or 8 is installed to the reactor to carry out the reactive distillation. This distillation column portion may be a column directly connected to the reactor, or an independent column of a system which is connected to a vapor piping from the reactor and a liquid supply piping from a distillation column, and thus the system is not particularly limited. Further, the heating system for the reactive distillation is not particularly limited and may be a coil type in the reactor, an internal multitubular heat exchanger type, an external jacket type or an external heat exchanger type.

In a case where the reactive distillation is carried out in a continuous system, the raw material may be supplied to the distillation column portion or the reactor portion at the bottom, but it is preferred to supply it to the distillation column portion.

Further, in the present invention, the byproduct formed during production of (meth)acrylic acid containing the Michael addition product, and the byproduct formed during production of a (meth)acrylic ester, may separately be subjected to thermal decomposition treatment, or they may be mixed and subjected to thermal decomposition treatment.

Embodiment d

Embodiment d is one wherein oxygen or an oxygen-containing gas is supplied directly to the distillate containing the decomposition product formed by the decomposition reaction of the above byproduct and one to suppress polymerization of an easily polymerizable compound in the decomposition product by the action of such oxygen. As a result of various studies, it has been found that polymerization of the easily polymerizable compound in the decomposition product can be sufficiently suppressed by the addition of such oxygen or an oxygen-containing gas. This is considered to be attributable to the fact that the oxygen added will increase the polymerization-suppressing effect of the polymerization inhibitor usually contained in the raw material for the decomposition reaction.

In Embodiment d, the (meth)acrylic ester is not particularly limited, but ones similar to those disclosed in Embodiment c may be mentioned. Further, with respect to the Michael-addition product, ones similar to those disclosed in Embodiment c may be mentioned.

The feed liquid (hereinafter sometimes referred to as the high boiling liquid) to be supplied to the reaction decomposition column also contains substances used or generated in the process for producing acrylic acid or acrylic esters. Specifically, they are acrylic acid, acrylic esters, maleic acid, maleic acid esters, furfural, benzaldehyde, polymers, oligomers, alcohols to be used as materials for production of esters, and a polymerization inhibitor (copper acrylate, copper dithiocarbamate, a phenol compound, a phenothiazine compound, etc.).

The above copper dithiocarbamate may be ones similar to those disclosed in Embodiment a. Further, the above phenol compound may be ones similar to those disclosed in Embodiment a.

Substances other than the above may sometimes be contained depending upon the process.

(Meth)acrylic acid in Embodiment d is the same as disclosed in Embodiment c. Further, the method for producing a (meth)acrylic ester in Embodiment d, for example, comprises a reaction step of reacting an alcohol to (meth)acrylic acid for esterification by using a cationic ion exchange resin as a catalyst, and a purification step of carrying out washing, extraction, evaporation, distillation or the like, to carry out separation of the catalyst, concentration, purification, etc. of the crude acrylic ester solution obtained in the reaction step. The raw material molar ratio of the (meth)acrylic acid or the (meth)acrylic ester to the alcohol in the reaction step, the type and amount of the catalyst to be used for the reaction, the reaction system, the reaction conditions, etc., are suitably selected depending upon the type of the alcohol raw material. The Michael addition product by-produced mainly in the esterification reaction step, will be concentrated as a heavy fraction at the bottom of a reaction column for recovering a variable component.

The byproduct formed during the production of acrylic acid and the byproduct formed during the production of an acrylic ester may be together decomposed.

In Embodiment d, any system of a continuous system, a batch system, a semi-batch system or an intermittent discharge system, may be employed for the reaction process to carry out the decomposition reaction of the Michael addition product, but a continuous system is preferred. Also the type of the reactor is not particularly limited, and any type such as a flow tubular type reactor, a thin film flowing down type reactor, a completely mixing tank type stirring tank reactor or a circulation type completely mixing tank type reactor, may be employed. To obtain useful components contained in the decomposition reaction product, a method of obtaining them by evaporation or distillation during the reaction or a method of obtaining them by evaporation or distillation after the decomposition reaction, may either be employed. However, in order to obtain a high recovery rate, the former reactive distillation system is preferred.

In the case where the reactive distillation system is employed, the reaction pressure depends substantially on the after-mentioned reaction temperature, and a pressure is employed such that the majority of useful components such as acrylic acid, an acrylic ester, an alcohol, etc., produced in the decomposition reaction and contained in the raw material for the decomposition reaction will be evaporated.

The catalyst may be selected from a Lewis acid, a Lewis base, an inorganic acid such as sulfuric acid or phosphoric acid, and an organic acid such as methanesulfornic acid or p-toluenesulfonic acid. Water may be supplied to the decomposition reaction column so that decomposition may be carried out in the coexistence of the high boiling fraction and water.

The concentration of the acid catalyst is preferably from 0.1 to 1.0 wt %, particularly preferably from 0.2 to 0.8 wt %, based on the charged liquid.

The decomposition reaction temperature is preferably from 110 to 250° C., particularly preferably from 120 to 230° C. The liquid retention time based on the discharge liquid is preferably from 0.5 to 50 hours. Further, in a case where the decomposition reaction temperature is lower, it is preferably from 10 to 50 hours, and in a case where the decomposition reaction temperature is higher, it is preferably from 0.5 to 10 hours. Further, in a case where the decomposition reaction is carried by a continuous reaction, with respect to the reaction time, the liquid retention time as calculated by the discharge liquid may be regarded as the reaction time. For example, in a case where the liquid capacity in the reactor is 500 L, and the discharge liquid amount is 100 L/hr, the retention time will be 5 hours.

To the distillate from the decomposition reaction column, oxygen or an oxygen-containing gas (hereinafter sometimes referred to as oxygen or the like) is added to prevent its polymerization. As the oxygen or the like, pure oxygen, a gas having oxygen diluted with an inert gas, air, or a gas having air diluted with an inert gas, may, for example, be employed. The inert gas may, for example, be nitrogen, carbon dioxide, argon or neon. The addition of the inert gas is to avoid formation of an explosive gas. The inert gas is preferably present in an amount of from 3.76 to 18.05 times by volume to oxygen, and in the case of air, the inert gas is preferably present in an amount of from 0.3 to 3 times by volume to air. From the viewpoint of costs, it is apparent that air is more inexpensive than oxygen. The oxygen or the like is preferably added in a proportion of from 0.0001 to 0.01 volume ratio, particularly from 0.0005 to 0.005 volume ratio as calculated as oxygen to the distilled gas.

Further, in the present invention, the addition of the oxygen or the like to the distilled gas of the decomposition reaction column, may be carried out to the line after discharge from the decomposition reaction column, or the oxygen or the like may be added to the top portion of the decomposition reaction column where the distilled gas is substantially formed.

Figure 11:
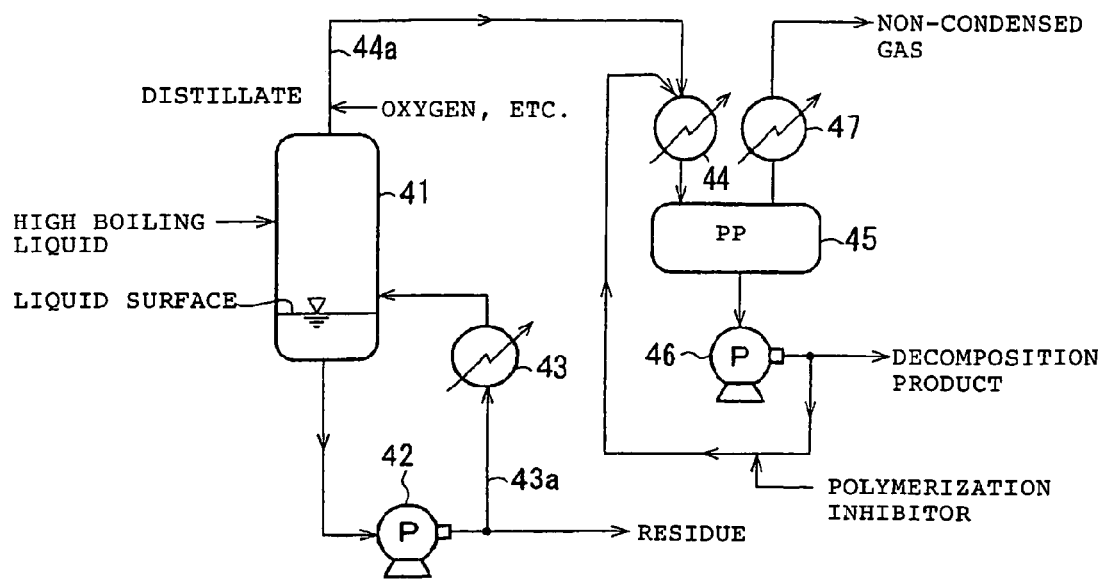
FIG. 11 is a flowchart for decomposition of a high boiling liquid.

FIG. 11 is a flowchart showing the decomposition reaction process. The high boiling liquid is supplied to a decomposition reaction column 41 and thermally decomposed. Here, this decomposition reaction column 41 may be provided with a stirrer to stir the liquid in the column. Further, the decomposition reaction column 41 may be provided with a jacket for heating employing steam or an organic heat medium as the heat source.

The bottom liquid in the decomposition reaction column 41 is withdrawn by a pump 42, and a part thereof is, via recycling line 43a, heated by a heat exchanger 43 for heating, and recycled, and the rest is discharged out of the system.

The distillate formed by the decomposition reaction is distilled from the top of the decomposition reaction column 41, and after addition of oxygen or the like, via a column top gas line 44a, cooled and liquefied by a heat exchanger 44 and introduced into a cooled liquid tank 5. Here, in a case where a reflux line is provided, the cooled liquid tank 45 may be omitted. In FIG. 11, the gas component in the cooled liquid tank 45 is led from the cooled liquid tank 45 to a heat exchanger 7 and cooled, whereby a valuable substance will be liquefied. The non-condensed gas will be supplied to a valuable substance-recovery installation or a vacuum installation (not shown). The liquid in the cooled liquid tank 45 is withdrawn via a pump 46, and a part thereof will be, after adding a polymerizing inhibitor, recycled via the heat exchanger 44 to the cooled liquid tank 45, and the rest will be taken out as the decomposition product. This decomposition product will be returned to the process for producing acrylic acid or an acrylic ester, as mentioned above.

In the decomposition reactor 41, trays or a packing material, which is commonly used in a distillation column, may be provided. In such a case, it will be operated as a decomposition reactive distillation column. As the packing material, a regular packing material such as SULZER PACKING manufactured by SULZER BROTHERS LTD., SUMITOMO SULZER PACKING manufactured by SUMITOMO HEAVY INDUSTRIES, LTD., MELLAPACK manufactured by SUMITOMO HEAVY INDUSTRIES, LTD., GEMPAK manufactured by GLITSCH, MONTZ PACK manufactured by MONTZ, GOODROLL PACKING manufactured by TOKYO TOKUSHU KANAAMI K.K., HONEYCOMB PACKING manufactured by NGK INSULATORS, LTD. or IMPULSE PACKING manufactured by NAGAOKA INTERNATIONAL CORPORATION, or an irregular packing material such as INTALOX SADDLE manufactured by NORTON, TELLERETTE manufactured by Nittetu Chemical Engineering Ltd., PALL RING manufactured by BASF, CASCADE MINI-RING manufactured by MASS TRANSFER or FLEXIRING manufactured by JGC CORPORATION, may be mentioned. Any one of these packing materials may be employed, or more than one type may be used in combination.

The trays may, for example, be bubble cap trays, perforated plate trays, bubble trays, superflux trays, max flux trays, etc. having a downcomer, or dual trays, etc. having no downcomer. The trays or the packing materials may be used in combination.

Further, no such a content may be provided in the decomposition reaction column. In such a case, a distillation column or the like may be installed, as the case requires.

In a case where a stirring means is provided in the decomposition reaction column 41, the stirring vanes may be of any type, and for example, they may be anchor vanes, (at least one stage) multistage paddle vanes, (at least one stage) multistage inclined paddle vanes, as special ones, MAXBLEND vanes (manufactured by SUMITOMO HEAVY INDUSTRIES, LTD.), or FULLZONE VANES (manufactured by SHINKO PANTEC CO., LTD.). More than one type may be used in more than one stage i.e. in multistages. Particularly preferred are anchor vanes or lattice vanes.

Baffle plates (baffles) to be installed together with the stirring vanes may be of any type. Specifically, they may be of a rod type, a plate type or a comb type, and more than one type, and more than one baffle may be installed. It is particularly preferred to install one rod type or one plate type. However, no baffle may be provided.

The fraction rich in (meth)acrylic acid, a (meth)acrylic ester and an alcohol, obtained by the decomposition reaction, is recovered in its entire amount for the step for producing an acrylic ester. The place where the recovered fraction is to be recycled, is not particularly limited. However, it contains a small amount of a light fraction, and accordingly, it is preferred to recycle it to a place prior to the step of separating the light fraction.

Embodiment e

The invention of this Embodiment e relates to a process for recovering acrylic acid. Particularly, in a process which comprises contacting acrylic acid containing maleic acid, particularly an acrylic acid-containing gas obtained by a vapor phase catalytic oxidation of propylene, with a solvent, to collect acrylic acid in the form of an acrylic acid-containing solution, distilling off a low boiling point component from the acrylic acid-containing solution by azeotropic distillation or direct distillation, then obtaining acrylic acid by fractionation, while thermally decomposing an oligomer of acrylic acid contained in the bottoms of a distillation column, and recovering acrylic acid and recycling it to a purification step, it relates to a method for efficiently removing maleic acid as an impurity from the liquid to be supplied to the thermal decomposition reactor or from the distillate.

The invention of Embodiment e has been accomplished on the basis of the discovery of the following fact by the present inventors.

Maleic acid formed together with acrylic acid by the oxidation reactor is present in the form of a dicarboxylic acid having two carboxyl groups, in an aqueous solution, but in acrylic acid, it may have a form of maleic anhydride having one molecule of water dehydrated from its molecule. Maleic acid and maleic anhydride are in an equilibrium state, and in the acrylic acid solution to be supplied to the recovery apparatus of the thermal decomposition reaction of an oligomer of acrylic acid, the concentration of water as a low boiling point component is low, whereby the equilibrium is substantially shifted to maleic anhydride.

When water is added to such a liquid, a part of maleic anhydride turns into maleic acid in correspondence with the amount of water added.

In the column top liquid (or gas) of the thermal decomposition reactor, water formed by the thermal decomposition of 3-hydroxypropionic acid, etc. is present, and a part of maleic anhydride will be reacted with this water to form maleic acid.

For the equilibrium reaction, it takes sometime, and the equilibrium will be accelerated by heating.

The solubility of maleic acid in acrylic acid is low as compared with maleic anhydride, and maleic acid is likely to undergo precipitation.

The degree of precipitation depends on the concentration of maleic acid or water in the liquid and the operation temperature, and by an addition of a water-insoluble solvent, precipitation will be accelerated.

It is possible to facilitate precipitation and separation by reducing the solubility by converting maleic anhydride to maleic acid in the liquid to be supplied to the thermal decomposition reactor for acrylic acid or in the recovered liquid from the thermal decomposition reactor.

And, by such a method, circulation in the purification system of maleic acid involved in the thermal decomposition and recovery of an oligomer of acrylic acid formed in the step for distillation and purification of the acrylic acid-containing liquid, can easily be reduced by precipitation and solid-liquid separation utilizing the chemical equilibrium of the acid and the acid anhydride, whereby it is made possible to recover acrylic acid without a problem of clogging by polymerization.

Now, Embodiment e will be described in detail with respect to each of items "Thermal decomposition reactor", "Preparation of acrylic acid solution", "Reaction of maleic acid", "Precipitation operation", and "Separation of the precipitate".

Thermal Decomposition Reactor

The bottom liquid of the purification (product) column for acrylic acid or the liquid obtained by concentrating and heating the bottom liquid by a thin film evaporator or the like, is used as the liquid to be supplied, and heat decomposition of an oligomer of acrylic acid is carried out within a temperature range of from 120 to 220° C. The step for the thermal decomposition reaction and the step for separating the decomposed products may be carried out in the same equipment such as a reactive distillation column, or in separate equipments, such as a combination of a heating tank and an evaporator. A catalyst may be used for the thermal decomposition reaction. As a type of the catalyst, a compound having a secondary or tertiary amino group, or a tertiary phosphine may, for example, be mentioned. However, the catalyst is not limited thereto. Otherwise, the decomposition reaction may be carried out in the absence of any catalyst.

Preparation of Acrylic Acid Solution

The liquid to be supplied to the thermal decomposition reactor or the recovered liquid from the thermal decomposition reactor (the distillate) is to be treated.

The concentration of maleic acid or/and maleic anhydride in the recovered liquid is within a range of from 1.6 to 28 wt %, preferably from 2.5 to 25 wt %. If the concentration of maleic acid is low, the precipitation tends to be difficult, and if the concentration is too high, the loss of acrylic acid increases at the time of separating the precipitated maleic acid.

The concentration of water is as follows in a molar ratio:

$$\frac{\text{Water}}{\text{Maleic acid} + \text{Maleic anhydride} \times 2} \leq 1.0$$

Particularly preferably, it is within a range of [maleic anhydride]×0.8≦[water]≦[maleic acid]×0.5+[maleic anhydride]. If the concentration of water is too high, the precipitation amount of maleic acid decreases, and the time required for precipitation will be long.

The concentration of acrylic acid is at least 70 wt %. If it is lower than this, the liquid nature will be different, and there will be a case where the effect of the present invention can not be obtained.

Reaction of Maleic Acid

In the solution, maleic acid and maleic anhydride are present. As compared with maleic anhydride, maleic acid has a low solubility in acrylic acid. Accordingly, the larger the ratio of maleic acid/maleic anhydride in the solution, the more efficient the removal by precipitation.

To accelerate formation of maleic acid by the reaction of maleic anhydride with water, the liquid temperature may be raised to from 50 to 70° C. If the temperature is raised beyond this range, the speed of the formation of an oligomer of acrylic acid will be accelerated, whereby not only the efficiency for heating, decomposition and recovery of the oligomer will decrease, but also polymerization of acrylic acid is likely to take place, such being undesirable.

The reaction tank to be used is not particularly limited. However, it is preferably provided with a system to stir the solution, such as stirring vanes or an external circulation by a pump, in order to prevent polymerization in the tank.

In a case where the amount of maleic acid (not including anhydride) in the solution exceeds 2 wt %, the above operation may be omitted.

Precipitation Operation

From the above-mentioned solution, maleic acid is precipitated. The tank to be used for such precipitation may be one used for the above operation or may be a separate tank. The time required for the precipitation is preferably within a range of from 0.5 to 5 hours including the above operation. If the time is too short, the precipitation efficiency tends to be poor. From the viewpoint of the efficiency, the longer the required time, the better. However, the instrument to be used is required to be large, such being uneconomical.

The operation temperature is from 20 to 70° C., preferably from 20 to 40° C. If the operation temperature is too low, the cooling load will be increased, such being uneconomical. Further, the melting point of acrylic acid is 13° C., and freezing of acrylic acid may occur. The higher the temperature, the more polymerizable the acrylic acid, and the solubility of maleic acid will increase, such being undesirable.

A solvent capable of forming double liquid layers with water, may be added, whereby the precipitation amount and the precipitation speed of maleic acid can be increased. The solvent which may be employed for this purpose, may, for example, be an aliphatic hydrocarbon such as heptene or octene, an aromatic hydrocarbon such as toluene, xylene or ethylbenzene, an ester such as isopropyl acetate, or a ketone such as methyl isobutyl ketone, but it is not limited thereto. More preferred is a low polarity solvent such as an aromatic or aliphatic hydrocarbon. The amount is preferably from 0.5 to 4 times by volume to the recovered acrylic acid solution. If the amount is too small, no adequate effects for the precipitation amount tends to be obtained. On the other hand, an excessive amount of addition increases a load to the process such as the size and ability of the instrument, such being uneconomical. The same one as the azeotropic agent to be used for the dehydration distillation step may be employed, and in such a case, the thermal load to remove the added solvent will not be substantially increased.

Stirring may be carried out to prevent deposition on the tank wall of crystals precipitated in the tank. Further, crystals having a uniform particle size will be precipitated by stirring, which makes the subsequent separation step easy.

Separation of the Precipitate

Separation of the precipitated maleic acid may be carried out in the tank used for precipitation. However, it is convenient to carry out the separation against the liquid withdrawn from the precipitation tank, so that the operation can be continuously carried out.

As a means for removing precipitated maleic acid in the discharged liquid, a change-over strainer may, for example, be convenient. However, such a means is not limited thereto, and a usual solid-liquid separator may be employed. A thickener, a precipitation tank, a cyclone, a strainer, a centrifugal separator or the like may be employed. The separated solid may be taken out by opening the instrument. However, it may be dissolved by a small amount of warm water and may be removed as waste water. Depending upon the instrument, the separated solid may continuously be discharged. The acrylic acid solution having the precipitate removed, contains water or an organic solvent added for the precipitation operation and therefore preferably recycled to a purification step prior to the purification column for acrylic acid.

As a result of the above operation, the concentration of maleic acid in the recovered acrylic acid will be reduced to a level of from 1.4 to 3 wt %. The content of this level will not adversely affect the purity of the product, even if recycled to the purification step.

Embodiment f

The invention of Embodiment f relates to a method for installing a liquid level meter to be used for the equipment for producing an easily polymerizable compound. More particularly, it relates to a method for installing a high pressure side detection portion of the liquid level meter and is directed to a method for installing a liquid level meter, whereby continuous operation of the equipment has been made possible without clogging of the detection portion of the liquid level meter.

Figure 12:
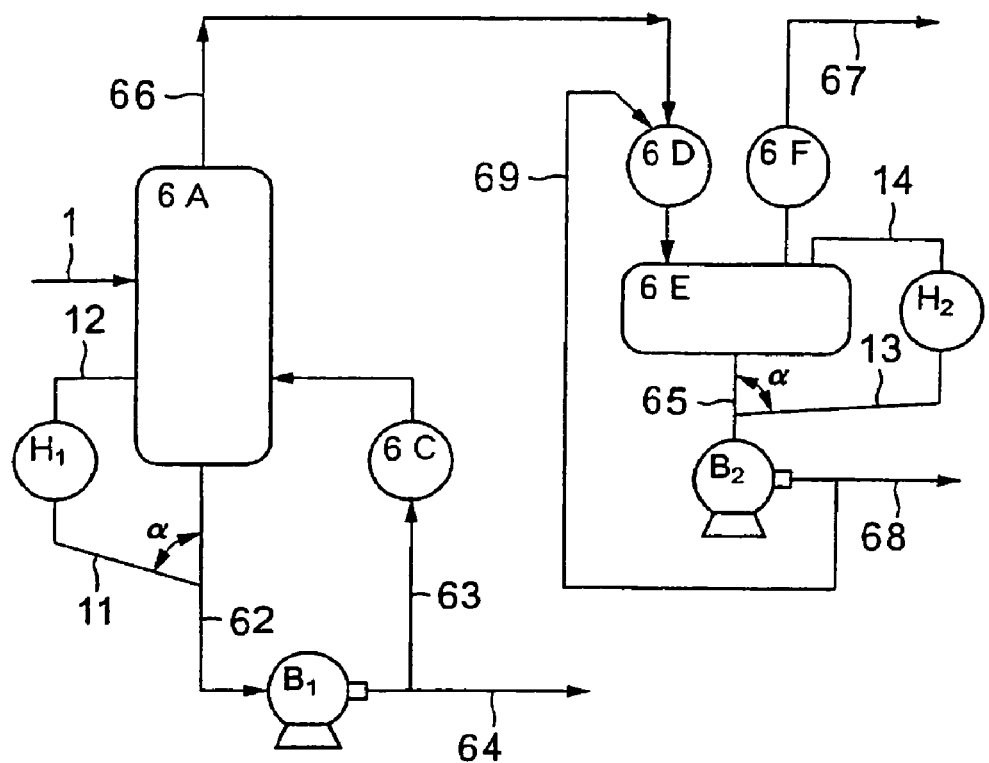
FIG. 12 is a view showing the entire installation wherein the method for installing a liquid level meter of the present invention is applied to a (high boiling material) decomposition reaction column and a top gas-cooled liquid tank in the production of acrylic acid.
Figure 13:
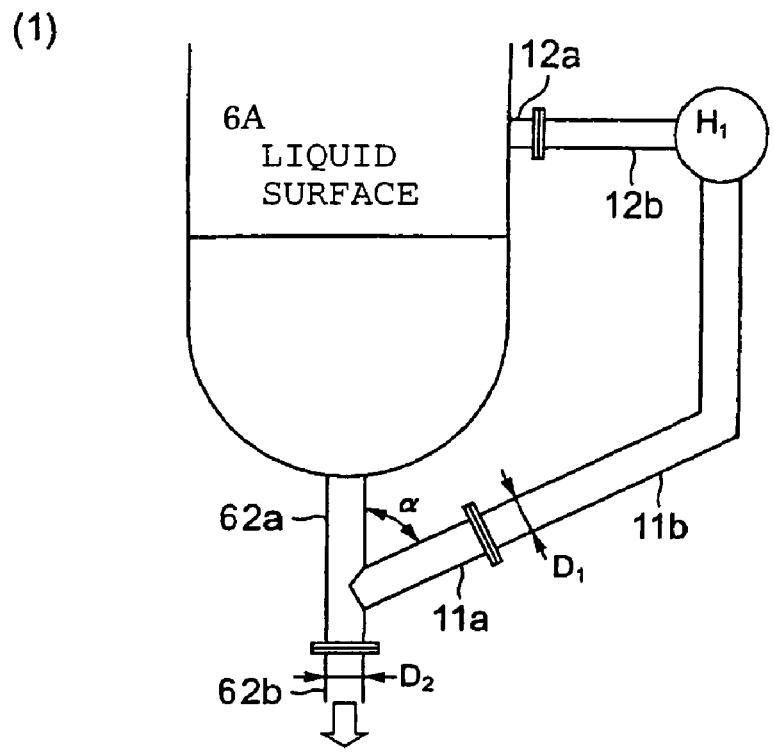
FIG. 13 is a partially enlarged view showing a liquid level meter installed on the (high boiling material) decomposition reaction column of FIG. 11.
Figure 13:
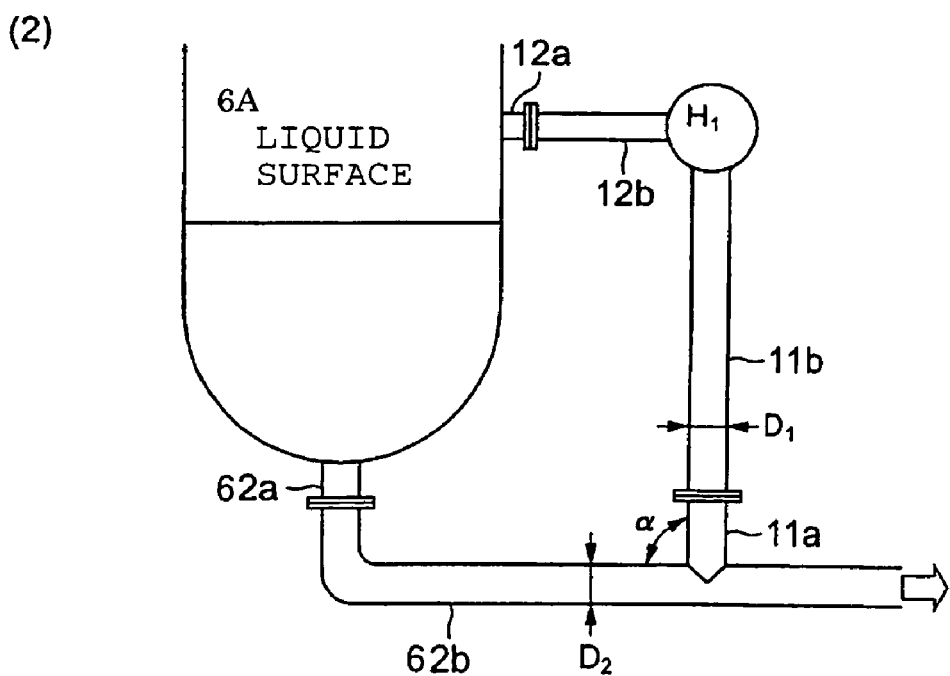
Figure 14:
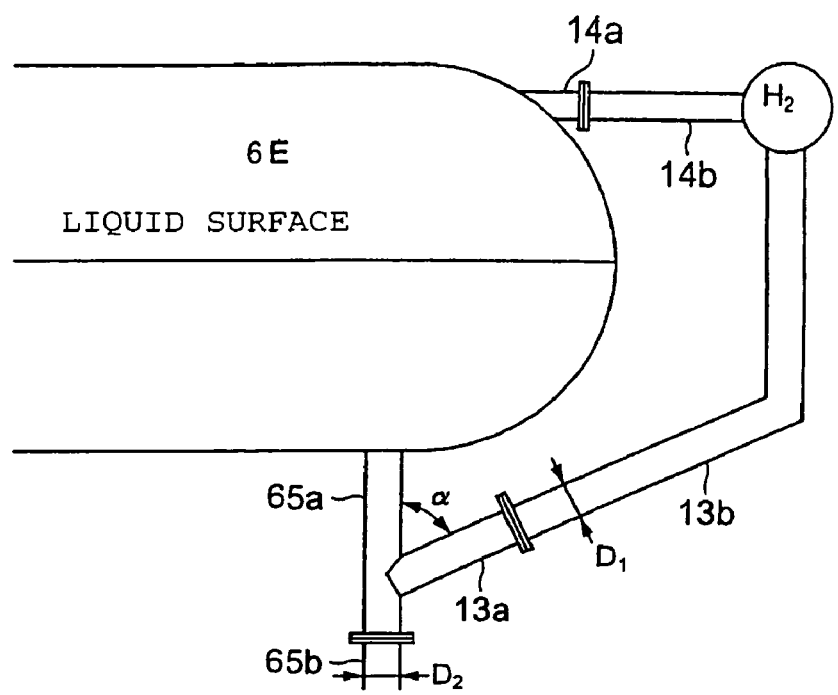
FIG. 14 is a partially enlarged view showing a liquid level meter installed on the top gas-cooled liquid tank of FIG. 11.
Figure 14:
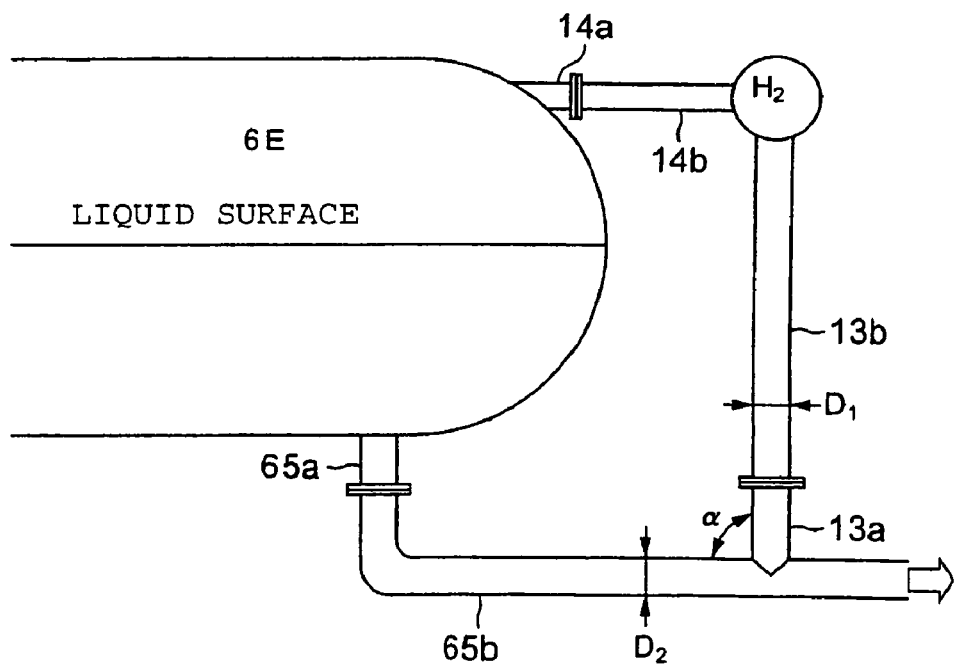

FIG. 12 is a view showing the entire installation wherein the method for installing a liquid level meter of the invention of Embodiment f is applied to the (high boiling material) decomposition reaction column and the top gas-cooled liquid tank in the production of acrylic acid, FIG. 13 is a partially enlarged view showing a liquid level meter installed on the (high boiling material) decomposition reaction column of FIG. 12, and FIG. 14 is a partially enlarged view showing a liquid level meter installed on the top gas-cooled liquid tank of FIG. 12.

Firstly, with reference to FIG. 12, the installation for the production of acrylic acid will be generally described. 6A is a (high boiling material) decomposition reaction column, and a supply line 61 is attached to the (high boiling material) decomposition reaction column 6A. $6B_1$ is a bottom pump, and the inflow side of the bottom pump $6B_1$ is connected to a bottom liquid discharge line 62 attached to the bottom of the (high boiling material) decomposition reaction column 6A, and its outflow side is connected to the decomposition residue discharge line 64.

6C is a heat exchanger for heating, and the inflow side of the heat exchanger for heating is connected to the supply line 63 for the heat exchanger for heating, branched from the decomposition residue discharged line 64, and its outflow side is connected to a lower side wall of the (high boiling material) decomposition reaction column 6A by a line.

6D is a heat exchanger for cooling the column top gas, and the inflow side of the heat exchanger 6D for cooling the column top gas is connected to a decomposition gas recovery line 66 attached to the top of the (high boiling material) decomposition reaction column 6A, and its outflow side is connected to the inflow side of a column top gas-cooled liquid tank 6E via a line.

Further, the outflow side of the column top gas-cooled liquid tank 6E is connected to a column top gas-cooled liquid discharge line 68 via a tank bottom liquid discharge line 65 and a pump $6B_2$, and the column top gas-cooled liquid is transferred by this line 68 to the next installation.

A cooled liquid return line 69 branched from the column top gas-cooled liquid discharge line 68, is connected to the inflow side of the heat exchanger 6D for cooling the column top gas.

6F is a heat exchanger for cooling a vent gas, and the inflow side of the heat exchanger 6F for cooling a vent gas, is connected to the column top gas-cooled liquid tank 6E via a line. The vent gas flowing into the heat exchanger 6F for cooling a vent gas, will be cooled and, after a valuable substance in the gas is recovered, will be led to a vent gas discharge line 67.

$H_1$ and $H_2$ are differential pressure type liquid level meters, and the method for installing such liquid level meters $H_1$ and $H_2$ is the essential feature of the present invention.

Namely, the high pressure side of the differential pressure type liquid level meter $H_1$ is connected to the bottom liquid discharge line 62 via a high pressure side detection line 11, and the low pressure side of the differential pressure type liquid level meter $H_1$ is connected to the lower side wall of the (high boiling material) decomposition reaction column 6A via a low pressure side detection line 12.

The high pressure side of the differential pressure type liquid level meter $H_2$ is connected to the tank bottom liquid discharge line 65 via a high pressure side detection line 13, and the low pressure side of the differential pressure type liquid level meter $H_2$ is connected to the upper side of the column top gas-cooled liquid tank 6E via a low pressure side detection line 14.

Now, specific examples of the method for installing the above differential pressure type liquid level meters $H_1$ and $H_2$ will be described in detail with reference to FIGS. 13 and 14.

In FIGS. 13(1) and (2), 6A is the (high boiling material) decomposition reaction column, and the liquid stored at the bottom of the (high boiling material) decomposition reaction column 6A is withdrawn out of the column by the bottom liquid discharge line 62 constituted by the bottom liquid discharge short pipe 62a attached to the column bottom and a bottom liquid discharge conduit 62b.

$H_1$ is the differential pressure type liquid level meter, and the high pressure side of the differential pressure type liquid level meter $H_1$ is connected to either the short pipe 62a or the conduit 62b constituting the bottom liquid discharge line 62, by the high pressure side detection line 11 constituted by a high pressure side detection short pipe 11a and a high pressure side detection conduit 11b.

The connection angle $\alpha$ between the high pressure side detection line 11 and the bottom liquid discharge line 62 is from 5 to 90°, preferably from 10 to 90°.

If the connection angle is less than 5°, connection is practically difficult, and if the connection angle exceeds 90°, the solid substance in the liquid is likely to flow into the high pressure side detection line 11, such being undesirable.

The dimensional ratio $D_2/D_1$ is from 1 to 20, preferably from 1.3 to 10, where $D_1$ is the pipe diameter of the high pressure side detection line, and $D_2$ is the pipe diameter of the liquid discharge line.

If the ratio $D_2/D_1$ is less than 1, the solid substance in the liquid is likely to flow into the high pressure side detection line 11, such being undesirable, and if $D_2/D_1$ exceeds 20, detection of the liquid level tends to be difficult.

The low pressure side of the differential pressure type liquid level meter $H_1$ is connected to the lower side wall of the (high boiling material) decomposition reaction column 6A by a low pressure side detection line 12 constituted by a low pressure side detection conduit 12b and a low pressure side detection short pipe 12a.

FIG. 13(1) is an example wherein the high pressure side detection line 11 is connected to the vertical portion of the bottom liquid discharge line 62, while FIG. 13(2) is an example wherein the high pressure side detection line 11 is connected to a horizontal portion of the bottom liquid discharge line 62.

In FIGS. 14(1) and (2), 6E is the column top gas-cooled liquid tank, and the liquid stored in the bottom of the column top gas-cooled liquid tank 6E is withdrawn out of the tank by the tank bottom liquid discharge line 65 constituted by a tank bottom liquid discharge short pipe 65a attached to the tank bottom and a tank bottom liquid discharge conduit 65b.

$H_2$ is the differential pressure type liquid level meter, and the high pressure side of the differential pressure type liquid level meter $H_2$ is connected to either the short pipe 65a or the conduit 65b constituting the tank bottom liquid discharge line 65, by a high pressure side detection line 13 constituted by a high pressure side detection short pipe 13a and a high pressure side detection conduit 13b.

Further, the low pressure side of the differential pressure type liquid level meter $H_2$ is connected to the upper side of the column top gas-cooled liquid tank E by a low pressure side detection line 14 constituted by a low pressure side detection conduit 14b and a low pressure side detection short pipe 14a.

The connection angle $\alpha$ between this high pressure side detection line 13 and the tank bottom liquid discharge line 65, and the dimensional ratio $D_2/D_1$ where $D_1$ is the pipe diameter of the high pressure side detection line 13, and $D_2$ is the pipe diameter of the tank bottom liquid discharge line 65, are acceptable, if they satisfy the relation between the high pressure side detection line 11 and the liquid discharge line 62, as described in detail with reference to the above example of FIG. 13.

Here, FIG. 14(1) is an example wherein the high pressure side detection line 13 is connected to a vertical portion of the tank bottom liquid discharge line 65, and FIG. 14(2) is an example wherein the high pressure side detection line 13 is connected to a horizontal portion of the tank bottom liquid discharge line 65.

The above liquid discharge line is connected to a place where the liquid containing an easily polymerizable compound is stored, such as a distillation column, a reflux tank for a distillation column, a decomposition reaction column, a thin film evaporator, a column top gas-cooled liquid tank, a vertical storage tank, a horizontal storage tank or a tank, and the high pressure side detection line of the liquid level meter is attached thereto, so that the liquid level can be measured.

Further, the liquid level meter to be used in the present invention may, for example, be a differential pressure type liquid level meter, a glass gauge type or tubular direct vision type liquid level meter or a displacement type level indicator.

It is preferred that an injection inlet of a gas and/or a liquid is connected to the high pressure side detection line and/or the low pressure side detection line of such a liquid level meter.

In a case where by some operational change, a solid substance in the liquid flows into such a detection line, it is possible to quickly discharge the solid substance by the gas and/or the liquid. Such a gas and/or a liquid may be supplied continuously or intermittently.

The gas to be used for this purpose is preferably air nitrogen, carbon dioxide or the like, and as the liquid, it is preferred to use the same liquid as the liquid flowing in the liquid discharge line, such as acrylic acid or an acrylic ester.

Further, it is preferred that such a portion is heated or warmed to prevent deposition of a solid substance in the liquid in the high pressure side detection line and/or the low pressure side detection line of the liquid level meter.

The easily polymerizable compound to be measured by means of the method for installing a liquid level meter of the present invention is effective when (meth)acrylic acid or its ester is to be produced.

Further, as the liquid to be measured by the liquid level meter, particularly effective is one containing at least one type selected from an acrylic acid dimer, β-(meth)acryloxypropionic acid esters, β-alkoxypropionic acid esters, β-hydroxypropionic acid and β-hydroxypropionic acid esters, by-produced during the production of (meth)acrylic acid or its ester.

EXAMPLES

Now, the present invention will be described in further detail with reference to Examples and Comparative Examples, but the present invention is by no means restricted by such Examples. Here, the analysis of the composition of the high boiling material was carried out in accordance with a usual method by means of gas chromatograph provided with a flame ionization detector (FID).

Example a1

A decomposition reaction of a high boiling material was carried out by the installation shown in FIG. 1. As the decomposition reactor, a column type reactor made of Hastelloy C and having an outer diameter of 600 mm and a length of 1800 mm, was used. As raw material, a high boiling material having the following composition was continuously supplied from the line 1 at a rate of 580 kg/hr.

| Composition of high boiling material (raw material) | |
|---|---|
| Butyl acrylate: | 22 wt % |
| Butyl β-butoxypropionate: | 67 wt % |
| Butyl acryloxypropionate: | 4 wt % |
| Butyl β-hydroxypropionate: | 2 wt % |
| Hydroquinone: | 3 wt % |
| Methoxyquinone: | 2 wt % |

Further, as a decomposition reaction catalyst, a 1 wt % sulfuric acid aqueous solution was supplied at a rate of 58 kg/hr (10 wt % to the raw material feed liquid), and a decomposition reaction was carried out under a reaction pressure of 100 kPa at a decomposition temperature of 190° C. for a retention time of 1 hour.

From the line 6 at the top, a valuable substance composed mainly of acrylic acid and butanol, was recovered at a rate of 438 kg/hr, while a reaction residue having the following composition was discharged out of the system via the line 4 at a rate of 200 kg/hr.

| Composition of reaction residue | |
|---|---|
| Butyl acrylate: | 11.0 wt % |
| Butyl β-butoxypropionate: | 68.5 wt % |
| Butyl acryloxypropionate: | 2.0 wt % |
| Butyl β-hydroxypropionate: | 0.3 wt % |
| Hydroquinone: | 8.7 wt % |
| Methoxyquinone: | 5.8 wt % |
| Butanol: | 0.8 wt % |
| Sulfuric acid: | 2.9 wt % |

From the line 2 of the reactor A, the bottom liquid was withdrawn at a rate of 35350 kg/hr, and from the line 5 (see FIG. 4) installed in a tangent direction to the reactor A, 350 kg/hr of the bottom liquid was returned to the reactor A by a flow rate control valve (not shown in FIG. 1) installed on the line 5. The rest of 34800 kg/hr was returned to the reactor A via the heat exchanger C for heating and the return line 3-2 for heating. At that time, a spiral flow was formed at the bottom of the reactor A by the return liquid from the line 5. Further, the pipe for the line 3 was 4B, and the pipe for the line 5 was 11/2 (1.5)B.

After carrying out a continuous operation for 6 months, the operation was stopped, and the interior of the decomposition reaction column was inspected. No accumulation was observed at the bottom of the decomposition reaction column. Further, during the operation, there was no clogging in the transport pipe for the reaction residue.

Comparative Example a1

An operation was carried out by the same apparatus (FIG. 1) as in Example a1 except that with respect to the connection of the line 5 to the decomposition reactor, it was installed in the column center direction i.e. not in the tangent direction. After the operation for 2 months, cavitation occurred suddenly in the pump B. The operation of the decomposition reaction column was terminated, and the interior was inspected, whereby accumulation of a solid substance was observed at the bottom of the decomposition reaction column. The state of the solid substance accumulated at the bottom of the decomposition reaction column, is shown in FIG. 5.

Example a2

Using the same apparatus (FIG. 1) as in Example a1, a high boiling material having the following composition was continuously supplied from the line 1 at a rate of 580 kg/hr.

| High boiling (raw material) composition | |
|---|---|
| Acrylic acid: | 45.3 wt % |
| Maleic acid: | 10.0 wt % |
| Acrylic acid dimer (acryloxypropionic acid): | 42.4 wt % |
| Hydroquinone: | 1.3 wt % |
| Phenothiazine: | 1.0 wt % |

A decomposition reaction was carried out under a reaction pressure of 72 kPa at a decomposition temperature of 190° C. for a retention of 1 hours. From the line 6 at the top, a valuable substance composed mainly of acrylic acid was recovered at a rate of 449 kg/hr, while a reaction residue having the following composition was withdrawn out of the system via the line 4 at a rate of 131 kg/hr.

| Composition of reaction residue | |
|---|---|
| Acrylic acid: | 8.0 wt % |
| Maleic acid: | 14.0 wt % |
| Acrylic acid dimer (acryloxypropionic acid): | 67.2 wt % |
| Hydroquinone: | 5.8 wt % |
| Phenothiazine: | 4.4 wt % |
| Oligomer and polymer: | 0.6 wt % |

The bottom liquid of the decomposition reaction column was withdrawn from a ¾B nozzle (line 2) installed at the lowest position of the bottom portion and supplied to the pump B. Via the pump B, it was withdrawn from the line 4 at a rate of 131 kg/hr, while to the line 3, it was supplied at a rate of 32000 kg/hr as a return liquid to the decomposition reaction column via the heat exchanger C for heating by a pipe having a diameter of 4B.

On the other hand, the bottom liquid of the decomposition reaction column was supplied as a return liquid by the pump B from the line 5 to form the flow in a circumferential direction in the decomposition reaction column. The pipe diameter of the line 5 was 11/2 (1.5)B, and the flow rate was 400 kg/hr, and the such a control was carried out by a flow rate control valve (not shown in FIG.) installed on the line 5.

After carrying out a continuous operation for 6 months, the operation was stopped, and the interior of the decomposition reaction column was inspected. No accumulation was observed at the bottom of the decomposition reaction column. Further, during the operation, no clogging was observed in the transport pipe of the reaction residue.

Comparative Example a2

An operation was carried out by the same installation as in Example a2 except that in Example a2, the connection of the line 5 to the decomposition reaction column was made in the center direction instead of in the tangent direction.

After the operation for 70 days, cavitation occurred suddenly at the pump B. The operation of the decomposition reaction column was stopped, and the interior was inspected, whereby accumulation of a solid substance was observed at the bottom of the decomposition reaction column. The state of the solid substance accumulated at the bottom of the decomposition reaction column, was as shown in FIG. 5.

Example a3

A decomposition reaction of the same high boiling material as in Example a2 was carried out by using a decomposition reaction column (without a baffle) as shown in FIG. 3 having anchor vanes installed as stirring vanes. The decomposition reaction column has a jacket and has a diameter of 600 mm and a height of 1000 mm, and the vane diameter of the anchor vanes was 540 mm. An operation was carried out under the same operation conditions as in Example a2 by adjusting the rotational speed of the anchor vanes to 20 rpm. Six months later, the operation was stopped, and the interior was inspected, whereby no accumulation of a solid substance was observed in the column. Further, no clogging was observed in the discharge line installed at the lowest portion of the column bottom during the same period.

Example b1

A decomposition reaction of a high boiling material was carried out by the installation shown in FIG. 6. As the decomposition reactor, a column type reactor made of Hastelloy C and having an outer diameter of 600 mm and a length of 1800 mm, was used. As the raw material, a high boiling material having the following composition was continuously supplied from a line 1 at a rate of 580 kg/hr.

| Composition of high boiling material (raw material) | |
|---|---|
| Butyl acrylate: | 22 wt % |
| Butyl β-butoxypropionate: | 69 wt % |
| Butyl acryloxypropionate: | 4 wt % |
| Butyl β-hydroxypropionate: | 2 wt % |
| Hydroquinone: | 2 wt % |
| Methoxyquinone: | 1 wt % |

Further, as a decomposition reaction catalyst, a 1 wt % sulfuric acid aqueous solution was supplied at a rate of 58 kg/hr (10 wt % to the raw material supply liquid), and a decomposition reaction was carried out under a reaction pressure of 100 kPa at a decomposition temperature of 190° C. for a retention time of 1 hour.

From the top of the column, a valuable substance composed mainly of acrylic acid and butanol, was recovered at a rate of 449.5 kg/hr, and on the other hand, from the column bottom, the reaction residue of the following composition was intermittently withdrawn at a rate of 188.5 kg/hr. Namely, the intermittent discharge control valve D shown in FIG. 6 was operated for a closing time of 75 seconds and an opening time of 5 seconds (the opening ratio: 6.3%).

The discharged liquid was sent to the reaction residue storage tank installed in a distance of 800 m by means of a pipe having a diameter of ¾B (inner diameter: 22.2 mm). A continuous operation was carried out for 3 months, but no clogging was observed in the transport pipe for the reaction residue. The results are shown in Table 1.

| Composition of the reaction residue | |
|---|---|
| Butyl acrylate: | 11.7 wt % |
| Butyl β-butoxypropionate: | 72.7 wt % |
| Butyl acryloxypropionate: | 2.1 wt % |
| Butyl β-hydroxypropionate: | 0.4 wt % |
| Hydroquinone: | 6.2 wt % |
| Methoxyquinone: | 3.1 wt % |
| Butanol: | 0.8 wt % |
| Sulfuric acid: | 3.1 wt % |

Further, the decomposition rates of the respective components in the high boiling material were as follows.

| | |
|---|---|
| Butyl β-butoxypropionate: | about 67 wt % |
| Butyl acryloxypropionate: | about 83 wt % |
| Butyl β-hydroxypropionate: | about 74 wt % |

Here, with respect to each component in the high boiling material, the decomposition rate is defined by [1-(discharged amount from the decomposition reactor)/(supplied amount to the decomposition reactor)]×100 (%).

Examples b2 to b4

A reaction residual liquid obtained by the same installation and operation as in Example b1, was sent to the reaction residue storage tank in the same manner as in Example b1 except that the intermittent discharge time, (opening ratio) was changed to the condition as shown in Table 1. Under any condition, no clogging was observed in the transport pipe as a result of the continuous operation for 3 months. Further, the decomposition ratio of the high boiling material was substantially the same as in Example b1 with respect to each component. The results are shown in Table 1.

Comparative Example b1

A reaction residual liquid obtained by the same installation and operation as in Example b1, was sent continuously to the same reaction residue storage tank as in Example b1. From about the fifth day after initiation of the operation, gradual decrease was observed in the transport amount of the reaction residual liquid. A mechanical shock was given to the pipe from the exterior, clogging was partially and temporarily resolved, but complete recovery of the transport amount was impossible. Thereafter, the discharge amount continuously decreased, and accordingly, the retention time in the decomposition reactor gradually increased. As a result, the liquid state of the reaction residue became highly viscous, and on the 25th day, the operation of the decomposition reactor had to be stopped. Further, the decomposition ratio of the high boiling material during the steady operation before stopping was substantially the same as in Example b1 with respect to each component. The results are shown in Table 1.

Examples b5 to b8

Using the same apparatus as in Example b1, a decomposition reaction was carried out by supplying a high boiling material having the following composition as the raw material at a rate of 580 kg/hr.

| Composition of high boiling material (raw material) | |
|---|---|
| Acrylic acid: | 46.0 wt % |
| Maleic acid: | 10.0 wt % |
| Acrylic acid dimer (acryloxypropionic acid): | 42.4 wt % |
| Hydroquinone: | 0.9 wt % |
| Phenothiazine: | 0.7 wt % |

The conditions of the decomposition reaction were a reaction pressure of 72 kPa, a decomposition temperature of 190° C. and a retention time of 1 hour, and no decomposition catalyst was supplied.

From the column top, a valuable substance composed mainly of acrylic acid was recovered at a rate of 449.5 kg/hr, while from the bottom, a reaction residue having the following composition was intermittently discharged at a rate of 130.5 kg/hr. Namely, the closing time and the opening time of the intermittent discharge control valve D as shown in FIG. 6, were set as shown in Table 2, and the operation was carried out.

The discharged liquid was sent to the reaction residue storage tank installed in a distance of 800 m by means of a pipe having a diameter of ¾B (inner diameter: 22.2 mm). A continuous operation was carried out for 3 months, whereby no clogging was observed in the transport pipe for the reaction residue. Further, the decomposition ratio of the acrylic acid dimer was about 72%. The results are shown in Table 2.

| Composition of the reaction residue | |
|---|---|
| Acrylic acid: | 9.0 wt % |
| Maleic acid: | 14.0 wt % |
| Acrylic acid dimer (acryloxypropionic acid): | 69.5 wt % |
| Hydroquinone: | 4.0 wt % |
| Phenothiazine: | 3.1 wt % |
| Oligomer and polymer: | 0.4 wt % |

Comparative Example b2

A reaction residual liquid obtained by the same installation and operation as in Examples b5 to b8, was continuously sent to the same reaction residue storage tank as in Examples b5 to b8. From about the 5th day from the initiation of the operation, gradual decrease was observed in the transport amount of the reaction residual liquid to the storage tank. A mechanical shock was given to the pipe from the exterior, whereby clogging was partially and temporarily resolved, but complete recovery of the transport amount was impossible. Thereafter, the discharge amount continuously decreased, and the retention time in the decomposition reactor gradually increased. As a result, the liquid state of the reaction residue became highly viscous, and the operation of the decomposition reactor had to be stopped on the 18th day. The results are shown in Table 2.

TABLE 1

| | | Examples | | | | Comparative Example |
|---|---|---|---|---|---|---|
| | | b1 | b2 | b3 | b4 | b1 |
| Intermittent discharge control valve | Opening time (sec) | 5 | 3 | 10 | 20 | Continuously open |
| | Closing time (sec) | 75 | 60 | 120 | 180 | 0 |
| | Opening ratio (%) | 6.3 | 4.8 | 7.7 | 10 | 100 |
| State of the transport pipe for the reaction residual liquid | | No clogging for 3 months | No clogging for 3 months | No clogging for 3 months | No clogging for 3 months | The transport amount gradually decreased, and on the 25th day, the decomposition reactor had to be stopped |

TABLE 2

|  |  | Examples | | | | Comparative Example |
|---|---|---|---|---|---|---|
|  |  | b5 | b6 | b7 | b8 | b2 |
| Intermittent discharge control valve | Opening time (sec) | 5 | 3 | 10 | 20 | Continuously open |
|  | Closing time (sec) | 60 | 40 | 90 | 120 | 0 |
|  | Opening ratio (%) | 7.7 | 7 | 10 | 14.3 | 100 |
| State of the transport pipe for the reaction residual liquid |  | No clogging for 3 months | No clogging for 3 months | No clogging for 3 months | No clogging for 3 months | The transport amount gradually decreased, and on the 18th day, the decomposition reactor had to be stopped |

Example c1

A decomposition reaction was carried out in accordance with the present invention by using as raw material a bottom liquid of a high boiling fraction separation column in a process for producing methyl acrylate, having the following composition:

| Composition of the bottom liquid | |
|---|---|
| Acrylate acid: | 20 wt % |
| β-hydroxypropionic acid: | 1 wt % |
| Methyl β-hydroxypropionate: | 8 wt % |
| β-acryloxypropionic acid: | 8 wt % |
| Methyl β-acryloxypropionate: | 7 wt % |
| β-methoxypropionic acid: | 41 wt % |
| Methyl β-methoxypropionate: | 12 wt % |
| Other high boiling components, etc.: | 3 wt % |

As a reactor portion at the bottom of the decomposition reaction distillation column, a stirring tank made of Hastelloy C having an internal diameter of 1000 mm and a height of 2000 mm, and a heat medium was supplied to an external jacket to control the reaction temperature at 200° C., and the reaction pressure was maintained at 130 kPa. Further, at the upper portion of this stirring tank reactor, a distillation column having an internal diameter of 400 mm and a height of 4000 mm and further a condenser, were connected, whereby a decomposition reaction was carried out by a reactive distillation system.

In the interior of the distillation column, as shown in FIG. 7, disk-shaped trays 2A having a diameter $D_1$ of 280 mm were installed in five stages with a distance of 600 mm from the uppermost portion to the lowermost portion, and in-between thereof, doughnut-shaped trays 2B with an opening having an inner diameter $D_2$ of 260 mm were installed in four stages with an equal distance.

The feeding position of the raw material liquid was above the uppermost stage disk, and the above-mentioned bottom liquid as the raw material was supplied at a rate of 150 kg/hr. The liquid retention time was controlled by the liquid level in the decomposition reactor, and adjusted so that the retention time based on the discharged liquid would be 10 hours. The operation was continued for 1 month at a decomposition reaction temperature of 200° C., whereby no increase of the differential pressure was observed, and it was possible to carry out the operation under a stabilized condition.

After the operation, the interior of the distillation column was visually observed, whereby no accumulation of a solid substance was observed. The discharge amount of the decomposition residue during this period was 76 kg/hr on average, and the composition was analyzed by gas chromatography, and the results were as follows.

| Composition of the residue | |
|---|---|
| Water: | 0.2 wt % |
| Methanol: | 0.2 wt % |
| Methyl acrylate: | 0.3 wt % |
| Acrylic acid: | 39 wt % |
| β-hydroxypropionic acid: | 0.3 wt % |
| Methyl β-hydroxypropionate: | 7 wt % |
| β-acryloxypropionic acid: | 4 wt % |
| Methyl β-acryloxypropionate: | 4 wt % |
| β-methoxypropionic acid: | 31 wt % |
| Methyl β-methoxypropionate: | 8 wt % |
| Other high boiling components, etc.: | 6 wt % |

Comparative Example c1

A decomposition reaction was carried out for 1 month by using the same apparatus, raw material and reaction conditions as in Example c1 except that as the distillation column portion, a distillation column packed with 2000 mm of a coil pack as a packing material instead of the disk-and-doughnut type trays, was used. There was no distinct difference from Example c1 with respect to the discharge amount or the composition of the residue, but during this period, the pressure difference between the top and the bottom of the distillation column gradually increased, and upon expiration of 1 month, an increase of differential pressure of 2.6 kPa was observed. Further, after 1 month, the operation was stopped, and the packing material was taken out and visually inspected, whereby a substantial amount of a solid substance was found to have deposited.

As is evident from the results of the above Examples and Comparative Examples, when the process of the present invention is employed, it is possible to carry out a continuous operation in a stabilized condition without a trouble of e.g. clogging or an increase in the differential pressure and to prevent deposition or accumulation of the solid substance.

Example d1

A decomposition reaction of a high boiling liquid was carried out by the installation as shown in FIG. 11. The decomposition reactor had a column diameter of 1000 mm and a column length of 2800 mm, and the material was Hastelloy C. The composition of the high boiling liquid was 22 wt % of butyl acrylate, 67 wt % of butyl β-butoxypropionate, 4 wt % of butyl acryloxypropionate, 2 wt % of butyl β-hydroxypropionate, 3 wt % of hydroquinone and 2 wt % of methoxyquinone, and the liquid was supplied at a rate of 580 kg/hr.

As a decomposition reaction catalyst, a 1 wt % sulfuric acid aqueous solution was supplied in a weight ratio of 10% to the supplied liquid, and the decomposition reaction was carried out under a reaction pressure of 100 kPa at a decomposition temperature of 190° C. for a retention time of 1 hour, whereby a decomposition gas comprising 45.8 wt % of butyl acrylate, 23 wt % of acrylic acid, 16 wt % of butanol, 11.9 wt % of water, 2.9 wt % of butyl β-butoxypropionate, 0.003 wt % of hydroquinone, 0.007 wt % of methoxyquinone and 0.39 wt % of others was obtained from the top of the decomposition reaction column at a rate of 437.9 kg/hr. To the heat exchanger for cooling the decomposition gas, the liquid obtained by cooling the decomposition gas was returned at a rate of 800 kg/hr.

As oxygen or the like, air at a rate of 3 Nm³/hr and nitrogen as a diluting inert gas at a rate of 3 Nm³/hr were supplied to the column top gas line 44a as shown in FIG. 11.

After carrying out a continuous operation for 3 months, the operation was stopped, and the interior of the decomposition reaction column was inspected. No polymer was observed in the interior of the decomposition reaction column or in the heat exchanger for cooling the column top gas.

Comparative Example d1

An operation was carried out by the same installation as in Example d1 except that as oxygen or the like, air at a rate of 6 Nm³/hr and nitrogen as a diluting inert gas at a rate of 6 Nm³/hr were supplied to the recycling line 43a prior to the heat exchanger 43 for heating, i.e. not to the column top gas line 44a.

After a continuous operation for 3 months, the operation was stopped, and the interior of the decomposition reaction column was inspected. A polymer was observed in the interior of the decomposition reaction column. No polymer was observed in the heat exchanger 44 for cooling the column top gas.

Comparative Example d2

An operation was carried out in the same manner as in Comparative Example d1, except that air was supplied at a rate of 3 Nm³/hr, and nitrogen as a diluting inert gas was supplied at a rate of 3 Nm³/hr.

After a continuous operation for 3 months, the operation was stopped, and the interior of the decomposition reaction column was inspected. A polymer was observed in the interior of the decomposition reaction column, but the amount was about ⅓ of the amount in Comparative Example d1. Further, a polymer was observed also in the heat exchanger for cooling the column top gas.

Example d2

Decomposition of a high boiling liquid was carried out by using the same apparatus as in Example d1. The composition of the high boiling liquid was 5.3 wt % of acrylic acid, 10 wt % of maleic acid, 42.4 wt % of an acrylic acid dimer (acryloxypropionic acid), 1.3 wt % of hydroquinone and 1 wt % of phenothiazine, and the liquid was supplied at a rate of 580 kg/hr.

The decomposition reaction was carried out under a reaction pressure of 72 kPa at a decomposition temperature of 190° C. for a retention time of 1 hour, whereby a decomposition gas comprising 85.1 wt % of acrylic acid, 8.7 wt % of maleic acid, 2.1 wt % of an acrylic acid dimer (acryloxypropionic acid), 0.03 wt % of hydroquinone and 4.07 wt % of others was obtained from the top of the decomposition reaction column at a rate of 449.5 kg/hr. To the heat exchanger for cooling the decomposition gas, the liquid obtained by cooling the decomposition gas was returned at a rate of 500 kg/hr.

As oxygen or the like, air was supplied at a rate of 2 Nm³/hr to the column top gas line 44a as shown in FIG. 11.

After carrying out a continuous operation for 3 months, the operation was stopped, and the interior of the decomposition reaction column was inspected. No polymer was observed in the interior of the decomposition reaction column or in the heat exchanger for cooling the column top gas.

Comparative Example d3

An operation was carried out by the same installation as in Example d1 except that as oxygen or the like, air was supplied at a rate of 3 Nm³/hr to the recycling line 3a.

After a continuous operation for 3 months, the operation was stopped, and the interior of the decomposition reaction column was inspected. A polymer was observed in the interior of the decomposition reaction column. Further, a polymer was also observed in the heat exchanger for cooling the column top gas.

Example e1

| Recovered liquid from the thermal decomposition reactor | |
|---|---|
| Acrylic acid: | 88 wt % |
| Acrylic acid dimer: | 1.1 wt % |
| Acrylic acid trimer: | 100 wt ppm |
| Maleic acid: | 1.5 wt % |
| Maleic anhydride: | 5.7 wt % |
| Water: | |

$$\frac{\text{Water}}{\text{Maleic acid} + \text{Maleic anhydride} \times 2} \text{(molar ratio)} = 0.34$$

Operation 20 ml of a liquid having the above composition was put into a test tube with a stopper and subjected to horizontal shaking in an oil bath at 70° C. for 2 hours with an amplitude of 3 cm at a cycle of 1 second. Then, toluene was added in an amount of two times by a volume ratio, and the mixture was left to stand still at 35° C. for 1 hour, whereupon a precipitated solid was separated. The separation of the solid was carried out at room temperature by vacuum filtration employing a filter paper of 1 µ mesh. The separated solid contained mixed crystals of 96% maleic acid and maleic anhydride, and acrylic acid and very small amounts of impurities impregnated therein. The concentration of maleic acid including maleic anhydride after the removal of the solid was 2.6 wt % as calculated by excluding the added toluene.

Example e2

Separation of a solid was carried out under the same conditions as in Example e1 except that no addition of toluene was carried out. The concentration of maleic acid including maleic anhydride after removing the solid was 3.2 wt %.

Example e3

An operation was carried out under the same conditions as in Example e1 by adding 0.08 wt % of water at the time of heating at 70° C. The amount of water at that time was:

$$\frac{\text{Water}}{\text{Maleic acid} + \text{Maleic anhydride} \times 2} \text{ (molar ratio)} = 0.38$$

The concentration of maleic acid including maleic anhydride after removing the solid was 2.4 wt %.

Comparative Example e1

An operation was carried out under the same conditions as in Example e2 except that 3 wt % of water was added at the time of heating at 70° C. The amount of water at that time was:

$$\frac{\text{Water}}{\text{Maleic acid} + \text{Maleic anhydride} \times 2} \text{ (molar ratio)} = 1.63$$

No precipitation of a solid was observed, and the concentration of maleic acid including maleic anhydride was unchanged at 7.2 wt %.

Example f1

A decomposition reaction of a high boiling liquid was carried out by the installation as shown in FIGS. 12 and 13.

The composition of the high boiling liquid was 22 wt % of butyl acrylate, 67 wt % of butyl β-butoxypropionate, 4 wt % of butyl acryloxypropionate, 2 wt % of butyl β-hydroxypropionate, 3 wt % of hydroquinone and 2 wt % of methoxyquinone, and the liquid was supplied at a rate of 580 kg/hr.

As a decomposition reaction catalyst, a 1 wt % sulfuric acid aqueous solution was supplied in a weight ratio of 10% to the supplied liquid, and the decomposition reaction was carried out under a reaction pressure of 100 kPa at a decomposition temperature of 190° C. for a retention time of 1 hour, whereby from the bottom, a reaction residue comprising 11.7 wt % of butyl acrylate, 68.5 wt % of butyl β-butoxypropionate, 2 wt % of butyl acryloxypropionate, 0.3 wt % of butyl β-hydroxypropionate, 8.7 wt % of hydroquinone, 5.8 wt % of methoxyquinone, 0.8 wt % of butanol and 2.9 wt % of sulfuric acid, was obtained at a rate of 200.1 kg/hr and discharged from the bottom.

The bottom liquid of the decomposition reaction column was discharged from the bottom liquid discharge line 62 attached to the lowermost position of the bottom portion. The liquid level meter $H_1$ at the bottom was a differential pressure type liquid level meter and was installed as shown in FIG. 13(1). The connection angle α between the high pressure side detection line 11 and the bottom liquid discharge line was set to be 45°.

After carrying out a continuous operation for 6 months, the operation was stopped, and the high pressure side detection short pipe 11a and the high pressure side detection conduit 11b of the high pressure side detection line 11 of the liquid level meter $H_1$, were inspected. As a result of such inspection, no deposition was observed in either one of them.

Comparative Example f1

An operation was carried out under the same conditions as in Example f1 except that the high pressure side detection line 11 of the differential pressure type liquid level meter $H_1$ was connected horizontally to the lower side wall of the decomposition reaction column 6A. After operation for 2 months, cavitation occurred suddenly in the bottom pump $B_1$. Immediately, the operation of the decomposition reaction column 6A was stopped, and the interior was inspected, whereby it was found that no liquid was present at the bottom portion of the decomposition reaction column 6A, and the indication of the liquid level meter $H_1$ was erroneous.

The high pressure side detection short pipe 11a and the high pressure side detection conduit 11b of the high pressure side detection line 11 of the liquid level meter $H_1$ were inspected, whereby the short pipe 11a and the conduit 11b were found to be clogged.

Comparative Example f2

An operation was carried out under the same conditions as in Example f1 except that the high pressure side detection line 11 of the differential pressure type liquid level meter $H_1$ was connected at a connection angle α of 45° to the lower side wall of the decomposition reaction column 6A.

After an operation for 3 months, cavitation occurred suddenly in the bottom pump $B_1$. Immediately, the operation of the decomposition reaction column A was stopped, and the interior was inspected, whereby it was found that no liquid was present at the bottom portion of the decomposition reaction column A, and the indication of the liquid level meter $H_1$ was erroneous.

The high pressure side detection short pipe 11a and the high pressure side detection conduit 11b of the high pressure side detection line 11 of the liquid level meter $H_1$ were inspected, whereby the short pipe 11a and the conduit 11b were found to be clogged.

Example f2

An evaporation operation satisfying the following conditions was carried out by using a thin film evaporator.

As a raw material (crude acryl monomer) composition, a mixture comprising 66.6 wt % of acrylic acid, 8.0 wt % of maleic acid, 25.0 wt % of an acrylic acid oligomer, 0.5 wt % of hydroquinone and 0.5 wt % of phenothiazine, was supplied at 85° C. at a rate of 3000 kg/hr.

The operation was carried out under a column top pressure of 9 kPa under a bottom pressure of 10 kPa at a column top temperature of 95° C. and a bottom temperature of 98° C., whereby from the top of the column, 53% of the supplied amount was withdrawn, and acrylic acid having a purity of at least 88 wt %, was obtained.

From the bottom, a mixture comprising 41.1 wt % of acrylic acid, 10.9 wt % of maleic acid, 46.16 wt % of an acrylic acid oligomer, 0.92 wt % of hydroquinone and 0.92 wt % of phenothiazine, was discharged.

The bottom liquid of the thin film evaporator was discharged by the bottom liquid discharge line attached to the lowermost position of the bottom portion. The liquid level meter at the bottom was a differential pressure type liquid level meter and installed as shown in FIG. 13(1). The connection angle α between the high pressure side detection line 11 and the bottom liquid discharge line was set to be 45°.

After carrying out a continuous operation for 6 months, the operation was stopped, and the high pressure side detection short pipe 11a and the high pressure side detection conduit 11b of the high pressure side detection line 11 of the liquid level meter, were inspected. As a result of such inspection, no deposition was observed in either one of them.

Comparative Example f3

An evaporation operation was carried out under the same conditions as in Example f2 except that the high pressure side detection line 11 of the differential pressure type liquid level meter was connected horizontally to the lower side wall of the thin film evaporator.

After operation for 1 month, cavitation occurred suddenly in the bottom pump. The operation of the thin film evaporator was stopped, and the interior was inspected, whereby it was found that no liquid was present in the thin film evaporator, and indication of the liquid level meter was erroneous.

The high pressure side detection short pipe 11a and the high pressure side detection conduit 11b of the high pressure side detection line 11 of the liquid level meter, were inspected, whereby the short pipe 11a and the conduit 11b were found to be clogged.

INDUSTRIAL APPLICABILITY a. According to the present invention, in a process for recovering a valuable substance by heating and decomposing a high boiling material containing a Michael addition product of (meth)acrylic acids, the decomposition reaction residue can be transported without clogging from the decomposition reactor to a storage tank, whereby a continuous operation for a long time will be possible.

b. Further, according to the process for decomposing a byproduct formed during production of (meth)acrylic acids of the present invention, at the time of recovering a valuable substance such as (meth)acrylic acid, a (meth)acrylic ester and an alcohol by thermally decomposing by a reactive distillation system a byproduct formed during production of (meth)acrylic acid and/or a byproduct formed during production of a (meth)acrylic ester, it becomes possible to carry out a continuous operation under a stabilized condition while preventing adhesion, deposition or accumulation of a solid substance and while maintaining the recovery rate of the valuable substance at a high level without bringing about a problem such as clogging or an increase of the differential pressure of the distillation column due to deterioration of the gas-liquid contact state. Yet, in the present invention, a distillation column having a very simple structure may be adopted, whereby there will be a merit that the construction costs will be very low as compared with other distillation columns employing trays or a packing material.

c. Further, according to the present invention, it is possible to carry out decomposition treatment of a Michael addition reaction product by-produced in the step for producing (meth)acrylic acid and/or a (meth)acrylic ester, under a stabilized condition, whereby (meth)acrylic acid, a (meth)acrylic ester and an alcohol, etc. can be recovered at a high recovery rate.

d. Further, according to the present invention, an acrylic acid-containing gas obtained by catalytic oxidation of propane or propylene, is contacted with a solvent to collect acrylic acid as an acrylic acid-containing solution, the obtained acrylic acid-containing solution is distilled to purify acrylic acid, while an acrylic acid oligomer from the bottom liquid containing the acrylic acid oligomer, obtained from the purification column, is thermally decomposed, and acrylic acid having a small content of maleic acid, can be recovered efficiently.

e. Further, if a method for installing a liquid level meter of the present invention is adopted in the installation for producing a easily polymerizable compound, it is possible to prevent a solid substance present in the liquid of the easily polymerizable compound from flowing into a high pressure side detection line of the liquid level meter. Accordingly, the detection portion of the liquid level meter will not be clogged by the liquid to be measured, whereby an accurate continuous measurement by the liquid level meter will be possible, whereby the installation can be operated over a long period of time.

The entire disclosures of Japanese Patent Application No. 2001-369636 filed on Dec. 4, 2001, Japanese Patent Application No. 2001-371608 filed on Dec. 5, 2001, Japanese Patent Application No. 2001-385168 filed on Dec. 18, 2001, Japanese Patent Application No. 2001-392058 filed on Dec. 25, 2001, Japanese Patent Application No. 2002-141162 filed on May 16, 2002 and Japanese Patent Application No. 2002-141194 filed May 16, 2002 including specifications, claims, drawings and summaries are incorporated herein by reference in their entireties.

What is claimed is:

1. A process for producing (meth)acrylic acids, comprising:
   decomposing in a decomposition reactor a high boiling mixture formed as a byproduct during the production of (meth)acrylic acids,
   forcibly imparting a liquid flow in the circumferential direction to a liquid reaction residue in the decomposition reactor;
   recovering (meth)acrylic acid or a (meth)acrylic acid ester; and
   discharging the liquid reaction residue; wherein
   the high boiling mixture contains a Michael addition product having water, an alcohol or (meth)acrylic acid added to a (meth)acryloyl group, and
   the decomposition reactor comprises a liquid level meter wherein a high pressure side detection line of the liquid level meter is connected to a liquid discharge line of the decomposition reactor.

2. The process of claim 1 wherein the discharging the liquid reaction residue is intermittent.

3. The process of claim 2 wherein a discharge stop time is from 5 seconds to 5 minutes and a discharge time is from 2 seconds to 5 minutes.

4. The process of claim 1 wherein the high boiling mixture formed as a byproduct during the production of (meth) acrylic acids is continuously supplied to the decomposition reactor.

5. The process of claim 1 wherein the recovering (meth) acrylic acid or a (meth)acrylic acid ester comprises carrying out distillation as well as thermal decomposition of the high boiling mixture in a distillation column which is internally provided with disk-and-doughnut type trays.

6. A process for producing (meth)acrylic acids, comprising:
  decomposing in a decomposition reactor a high boiling mixture formed as a byproduct during the production of (meth)acrylic acids,
  forcibly imparting a liquid flow in the circumferential direction to a liquid reaction residue in the decomposition reactor;
  recovering (meth)acrylic acid or a (meth)acrylic acid ester; and
  discharging the liquid reaction residue; wherein
  the high boiling mixture contains a Michael addition product having water, an alcohol or (meth)acrylic acid added to a (meth)acryloyl group, and
  the liquid flow in the circumferential direction is imparted by a liquid supplied from the exterior of the decomposition reactor.

7. The process of claim 6 wherein the liquid supplied from the exterior of the decomposition reactor is the high boiling material supplied as raw material, or a return liquid of the liquid reaction residue discharged from the decomposition reactor.

8. The process of claim 6 wherein the recovering (meth) acrylic acid or a (meth)acrylic acid ester comprises carrying out distillation as well as thermal decomposition of the high boiling mixture in a distillation column which is internally provided with disk-and-doughnut type trays.

9. The process of claim 6 wherein a gas comprising oxygen is added to a distillate from the decomposition reactor.

10. The process of claim 6 wherein the decomposition reactor comprises a liquid level meter wherein a high pressure side detection line of the liquid level meter is connected to a liquid discharge line of the decomposition reactor.

11. The process of claim 6 wherein the discharging the liquid reaction residue is intermittent.

12. The process of claim 11 wherein a discharge stop time is from 5 seconds to 5 minutes and a discharge time is from 2 seconds to 5 minutes.

13. A process for producing acrylic acid, comprising:
  contacting with a solvent an acrylic acid-containing gas obtained by catalytic oxidation of propane or propylene,
  collecting acrylic acid in the form of an acrylic acid-containing solution, and
  purifying acrylic acid by distillation of the obtained acrylic acid-containing solution,
  recovering acrylic acid,
wherein the recovering acrylic acid comprises:
  precipitating and separating maleic acid from a bottom of a fractionating column for acrylic acid, or a liquid obtained by heating and concentrating such bottoms;
  supplying the bottom of a fractionating column for acrylic acid, or a liquid obtained by heating and concentrating such bottoms, from which the maleic is precipitated and separated, to a thermal decomposition reactor;
  decomposing an oligomer of acrylic acid in the liquid; and
  recovering the obtained acrylic acid in a purification step.

14. The process of claim 13, further comprising:
  precipitating maleic acid at from 20 to 700° C. within a range of from 0.5 to 5 hours;
  filtering and separating the maleic acid; and
  adjusting a composition of the liquid to be supplied to the thermal decomposition reactor or the liquid recovered from the thermal decomposition reactor, to at least 70 wt % of acrylic acid, from 1.6 to 28 wt % of maleic acid and/or maleic anhydride and water having a molar ratio of:

$$\frac{\text{Water}}{\text{Maleic acid} + \text{Maleic anhydride} \times 2}\text{(molar ratio)} \leq 1.0.$$

15. The process of claim 14, wherein an aliphatic or aromatic hydrocarbon is added in a volume ratio of from ½ to 4 times during the filtering and separating the maleic acid.

16. The process of claim 15, wherein the aliphatic or aromatic hydrocarbon is a solvent to be used for collecting the acrylic acid-containing gas, or an azeotropic agent to for dehydration distillation and purification of acrylic acid.

* * * * *